United States Patent [19]
Morrison et al.

[11] Patent Number: 5,489,668
[45] Date of Patent: Feb. 6, 1996

[54] IMMUNOASSAY REAGENTS AND METHOD FOR DETERMINING CYCLOSPORINE

[75] Inventors: Marjorie A. Morrison, Grayslake; Steven E. Lunetta, Waukegan; Victoria P. Meucci; Mariola B. Zajac, both of Chicago; Elizabeth A. Simpson, Skokie, all of Ill.

[73] Assignee: Abbott Laboratories, Abbott Park, Ill.

[21] Appl. No.: 148,164

[22] Filed: Nov. 4, 1993

Related U.S. Application Data

[63] Continuation of Ser. No. 952,488, Sep. 28, 1992, abandoned, which is a continuation of Ser. No. 567,842, Aug. 15, 1990, abandoned.

[51] Int. Cl.$^6$ .................................................. C07K 7/64
[52] U.S. Cl. ........................................ 530/321; 530/317
[58] Field of Search .................................. 530/317, 321

[56] References Cited

U.S. PATENT DOCUMENTS

| | | | |
|---|---|---|---|
| 3,969,287 | 7/1976 | Jaworek et al. | 530/816 |
| 4,117,118 | 9/1978 | Harri et al. | 514/11 |
| 4,289,851 | 9/1981 | Traber et al. | 435/71.1 |
| 4,727,035 | 2/1988 | Mahoney | 436/518 |
| 4,939,264 | 7/1990 | Heiman et al. | 436/537 |
| 5,106,951 | 4/1992 | Morgan et al. | 530/391.9 |
| 5,124,457 | 6/1992 | Ungeimach et al. | 546/196 |
| 5,239,057 | 8/1993 | Wang et al. | 530/321 |

FOREIGN PATENT DOCUMENTS

| | | |
|---|---|---|
| 0283801A2 | 9/1988 | Germany. |
| WO86/02080 | 10/1986 | WIPO. |

OTHER PUBLICATIONS

"Antibodies to Cyclosporine A (CsA) By A Novel Route And Their Use To Monitor Cyclosporine Levels By Radioimmunoassay (RIA)", Journal of Immunological Methods, 118 (1989) 257–263, Cacalano et al.
"Evaluation Of A New Automated Method For Cyclosporine A Therapeutic Monitoring On TDx Abbott", Analytical Letters, 22 (13 & 14), 2717–2736 (1989).
"Pharmacodynamics Of Cyclosporine In Patients Undergoing Bone Marrow Transplantation", Transplantation Proceeds vol. XVIII, No. 4 (Aug.), 1986: pp. 774–776.
"Metabolites of Cyclosporine", Transmplantation Proceedings, vol. XX, No. 2, Suppl 2 (Apr., 1988: pp. 575–584.
"A Radioreceptor Assay For The Measurement Of Cyclosporine Activity: A Preliminary Report", Therapeutic Drug Monitoring, 11:696–700 1989 Raven Press, Ltd. New York.
"Fine Specificity And Cross–Reactivity Of Monoclonal Antibodies To Cyclosporine", Molecular Immunology, vol. 24, No. 11, pp. 1159–1168, 1987.
"Disposition Of Cyclosporine In Several Animal Species And Man", The American Society for Pharmacology and Experimental Therapeutics, vol. 12, No. 1, pp. 120–126 (1984).
"Study Of The Confirmation Of Cyclosporine In Aqueous Medium By Means Of Monoclonal Antibodies" Int. J. Peptide Protein Res. 31, 1988 173–185.
122. Die Struktur von Ctyclosprin C, Helevetica Chimica Acta, vol. 60, Fasc 4 (1977) 122, pp. 1247–1255.
"Cyclosporine Metabolites Supress T Cell Proliferation Induced By Concanavalin A", Transplantation Proceedings, vol. XIX, No. 4 (Aug.), 1987: pp. 3490–3493.
"Critical Issues In Cyclosporine Monitoring: Report Of The Task Formce On Cyclosporine Monitoring", Clin. Chem 33/7, 1269–1288 (1987).
"Improved Liquid–Chromatographic Determination Of Cyclosporine, With Concomitant Detection Of A Cell–Bound Metabolite", Clin. Chem. 31.2, 196–201 (1985).
"Potential Of Monoclonal Antibodies To Improve Therapeutic Monitoring Of Cyclosporine", Clin. Chem. 33/1, 32–37 (1987).
"Derivatives Of Cyclosporin Compatible With Antibody–Based Assays: 1. The Generation of [$^{125}$I]–Labeled Cyclosporin", Clin. Chem. 31/3, 459–462 (1985).
"Cyclosporine Monitoring", Drug Intelligence and Clinical Pharmacy, Sep., 1986, vol. 20 pp. 649–652.
"A Radiommunoassay To Measure Cyclosporin A In Plasma And Serum Samples", Journal of Immunoassay, 291), 19–35 (1981).
"An Enzyme Immunoassay For The Searching Of Monoclonal Antibodies To Cyclosporin", Immunology Letters, 9 (1985) 99–104.
"Isolation And Structure Determination Of The New Cyclosproins E. F, G, H und I", Helvetica Chimica Acta, vol. 65, Fasc, 5 (1982), Nr. 162, 1655–1677.
Rudinger, Peptide Hormones, Parsons (Ed.), U. Park Press, Baltimore, pp. 1–7 (1976).
Cram and Hammond, "Organic Chemistry", 2nd edition, McGraw–Hill Book Company, New York, pp. 303–305 (1994).
Waldmann, Science, vol. 252, pp. 1657–1662 (1991).
Robins, Immunology in Plant Sciences, Linskens et al. (eds), Springer–Verlag, New York, pp. 86–141 (1986).
Kitagawa et al., J. Biochem. vol. 79, pp. 233–236 (1976).
Myers et al., Journal of Immunological Methods, vol. 121, pp. 129–142 (1989).

(List continued on next page.)

*Primary Examiner*—Christina Y. Chan
*Attorney, Agent, or Firm*—John F. Levis

[57] ABSTRACT

Cyclosporine derivatives useful as detectable tracer compounds for the immunoassay determination of cyclosporine are disclosed. The cyclosporine derivatives comprise a detectable moiety coupled to the amino acid at the first position (MeBmt) in cyclosporine, the second position (Abu) in cyclosporine, the third position (Sar) in cyclosporine, the eighth position (D-Ala) in cyclosporine, or the tenth position (MeLeu) in cyclosporine. A preferred cyclosporine derivative comprises a fluorescent moiety coupled to the hydroxyl group of the amino acid at the first position in cyclosporine, and is especially useful for the fluorescent polarization immunoassay deterimination of cyclosporine. A fluorescent polarization immunoassay method and test kit are also disclosed.

5 Claims, 2 Drawing Sheets

OTHER PUBLICATIONS

Dell'Arciprete et al., The Journal of Immunology, vol. 140, pp. 2466–2471 (1988).

Catalog of Clon–Pure Chemicals for Biotechnology, Clontech, pp. C1–C3, 1987.

Rüegger et al., Helvetica Chimica Acta–vol. 59 No. 112 pp. 1075–1092 (1976).

Donatsch et al., Journal of Immunoassay, vol. 2(1) pp. 19–32 (1981).

Fois et al., Journal of Pharmaceutical Sciences, vol. 80, No. 4, pp. 363–367 (1991).

IMMUNOASSAY REAGENTS AND METHOD FOR DETERMINING CYCLOSPORINE

This application is a continuation of application Ser. No. 07/952,488 filed Sept. 28, 1992, now abandoned, which a continuation of application Ser. No. 07/567,842 filed Aug. 15, 1990 now abandoned.

FIELD OF THE INVENTION

The present invention relates to reagents for determining the presence or amount of cyclosporine in a test sample. In particular, the present invention relates to detectable tracer compounds for use in immunoassays, especially fluorescent polarization immunoassays, for detecting the presence or amount of cyclosporine and metabolites of cyclosporine in a test sample.

BACKGROUND OF THE INVENTION

Cyclosporine is a cyclic undecapeptide of fungal origin [U.S. Pat. No. 4,117,118; Ruegger, et al., *Helvetica Chimica Acta*, Vol. 59 (4), pages 1075–1092 (1976); U.S. Pat. No. 4,289,851; and Traber, et al., *Helvetica Chemica Acta*, Vol. 60 (4), pages 1247–1255(1977) and Vol. 65 (5), pages 1655–1677(1982)] which is commonly employed as a potent immunosuppressive agent to prevent the rejection of transplanted organs such as kidney, heart, bone marrow, and liver in humans. The effectiveness of cyclosporine has also been investigated in the treatment of conditions such as psoriasis, conjunctivitis, arthritis, nephritis and autoimmune diseases [Donnelly, et al., *Therapeutic Drug Monitoring*, Vol. 11 (6), pages 696–700(1989)]. While a certain level of cyclosporine must be maintained in the bloodstream to prevent rejection of transplanted organs, nephrotoxicity, hepatotoxicity, and other side effects can result from higher blood levels of the drug or from prolonged exposure. Moreover, distribution and metabolism of cyclosporine varies greatly between individuals as well as in a single individual during the course of therapy. Accordingly, it is necessary to monitor the concentration or level of cyclosporine in biological fluids such as whole blood, plasma, and serum, for proper patient management [Burchart, et al., *Drug Intelligence and Clinical Pharmacy*, Vol. 20, pages 649–652(1986) and Shaw, et al., *Clinical Chemistry*, Vol. 33 (7), pages 1269–1288(1987)]. Measurement of cyclosporine in blood, plasma and serum has been complicated, however, by the presence of metabolites of cyclosporine therein [Maurer, et al., *Drug Metabolism and Disposition*, Vol. 12 (10), pages 120–126(1984)], and the toxicities, immunosuppressive activities, and synergistic effects of these metabolites are being investigated [Dindzans, et al., *Transplantation Proceedings*, Vo. 19 (4), pages 3490–3493 (1987); Yee, et. al., *Transplant. Proc.*, Volume 18, pages 774–776(1986); and Ryffel, et. al., *Transplant. Proc.*, Volume 20 (supplement 2), pages 575–584 (1988)]. Although the measurement of cyclosporine independently from its metabolites is desirable, there is also the need for assays that measure the metabolites as well as the parent drug (Donnelly, et al., supra). The metabolites of cyclosporine that have been identified in which the ring is still intact result from the hydroxylations and demethylations of the parent compound [Maurer, et al., *Drug Metabolism and Disposition*, 12 (1), pages 120–126 (1984)]. The structures of cyclosporine and some of its major metabolites are of the formula:

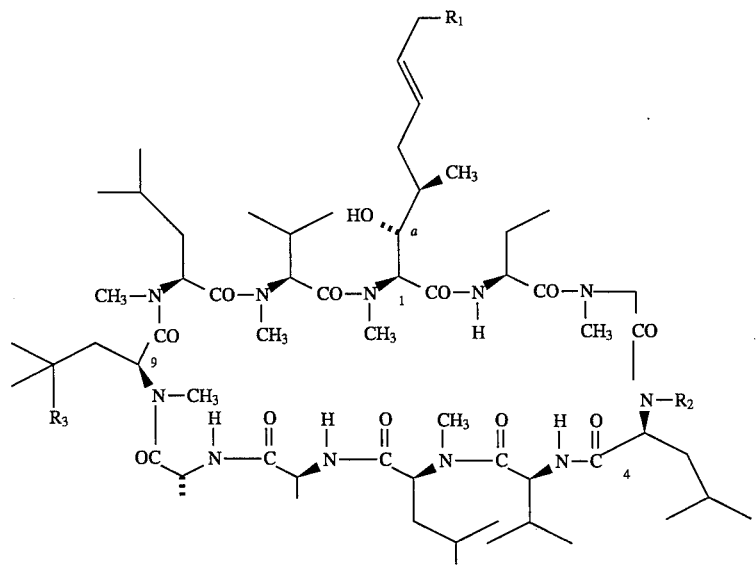

| METABOLITE | $R_1$ | $R_2$ | $R_3$ |
|---|---|---|---|
| Cyclosporine | H | $CH_3$ | H |
| AM9 (M-1) | H | $CH_3$ | OH |
| AM19 (M-8) | OH | $CH_3$ | OH |
| AM1 (M-17) | OH | $CH_3$ | H |
| AM1c (M-18) | * | $CH_3$ | H |
| AM4N (M-21) | H | H | H |

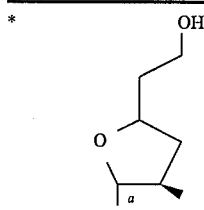

Modification of amine acid 1 in M-18

The structure of cyclosporine may be alternately represented by the formula:

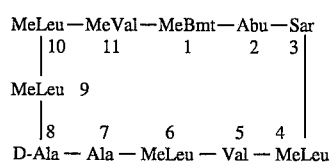

wherein "MeBmt" respresents a residue of N-methyl-(4R)-4-but-2E-en-1-yl-4-methyl-(L)-threonine; "MeVal" represents a residue of (N)-methyl-(L)-valine; "MeLeu" represents a residue of (N)-methyl-L-leucine; "D-Ala" represents a residue of D-alanine; "Ala" represents a residue of L-alanine; "Val" represents a residue of L-valine; "Abu" represents a residue of L-(alpha)-aminobutyric acid; and "Sar" represents a residue of sarcosine, also known as N-methylglycine. The term "residue" refers to the condensed form of the amino acid found in peptides, and the configuration of the alpha-amino acid is assumed to be L unless a D-configuration is specified. Conventional nomenclature for analogs of cyclosporine are defined herein by reference to the structure of cyclosporine (i.e., cyclosporin A) by first indicating those residues in the molecule which differ from those present in cyclosporine, and then applying the term "cyclosporine" to characterize the remaining residues which are identical to those present in cyclosporine. Thus, [Thr]$^2$ cyclosporine designates the cyclosporine in which the amino acid residue in the 2 position is threonine, i.e., cyclosporin C.

Cyclosporine levels in whole blood, plasma and serum have been measured by high performance liquid chromatogaphy (HPLC) [Lensmeyer, et al., Clinical Chemistry, Vol. 31(2), pages 196–201 (1985)], radioimmunoassay (RIA) utilizing $^3$H [Donatsch et al., Journal of Immunoassay, Vol. 2(1), pages 19–32 (1981)] or $^{125}$I [U.S. Pat. No. 4,727,035and Mahoney, et al., Clinical Chemistry, Vol. 31(3), pages 459–462 (1985)], fluorescent immunoassays (U.S. Pat. No. 4,727,035), and by fluorescence polarization immunoassay (FPIA) [Marty, et al., Analytical Letters, Vol. 22(13 & 14), pages 2717–2736 (1989) and European Patent Application Publication No. 283,801]. While the metabolites of cyclosporine can be distinguished from cyclosporine itself according to such HPLC methods, HPLC is nevertheless time and labor intensive, requiring extensive sample preparation and at least thirty minutes to perform the assay. Similarly, RIA assays suffer from the disadvantages of using radioactive materials which require special storage, handling and disposal, and typically require a minimum of two hours to perform.

While fluorescent polarization immunoassays are superior to the methods described above, particularly in ease of use, commercially available polyclonal antibody immunoassays display a lack of specificity for cyclosporine over its metabolites. In this regard, the specificity of immunoassays is dependent upon the antibody used, and the relative affinities of the antibody for cyclosporine, metabolites of cyclosporine, and the labeled form of cyclosporine. Recently, monoclonal antibodies specific for cyclosporine over its metabolites have been described [Quesniaux, et al., Immunology Letters, Vol. 12(1), pages 120–126 (1985), Clinical Chemistry, Vol. 33(1), pages 32–37 (1987), and Molecular Immunology, Vol. 24(11), pages 1159–1168 (1987)], and RIA assays using these antibodies have been found to correlate well with HPLC.

The present invention overcomes the disadvantages of the HPLC and RIA methods described above by providing reagents which are particularly useful in immunoassays, especially fluorescent polarization immunoassays, for detecting cyclosporine or cyclosporine and metabolites of cyclosporine. Moreover, the present invention is an advance over immunoassays for cyclosporine which have been previously described by providing novel tracer compounds for use in immunoassays, particularly fluorescent polarization immunoassays, employing either specific or nonspecific antibodies to detect cyclosporine or cyclosporine and metabolites of cyclosporine in a test sample.

SUMMARY OF THE INVENTION

The present invention relates to novel cyclosporine derivative compounds comprising cyclosporine, or analogs of cyclosporine, labeled with a detectable moiety for use as a tracer compound in an immunoassay for determining the presence or amount of cyclosporine, or cyclosporine and metabolites thereof, in a test sample. Preferably, the detectable moiety is fluorescein, or a derivative of fluorescein, wherein such fluorescent tracer compounds are particularly useful for performing fluorescent polarization immunoassays.

The cyclosporine derivatives of the present invention comprise a detectable moiety coupled to cyclosporine, or derivatives of cyclosporine, at the amino acids found at the first position (N-methyl(4R)-4-but-2E-en-1-yl-methyl-L-threonine residue)in cyclosporine, the second position (L-alpha-aminobutyric acid residue) of cyclosporine, the third position (N-methylglycine residue) of cyclosporine, the eighth position 8 (D-alanine residue) of cyclosporine, or the tenth position (N-methyl-L-leucine residue) of cyclosporine, preferably to the hydroxyl group of the amino acid at the second position of cyclosporine.

Preferred cyclosporine derivatives of the present invention are of the structures:

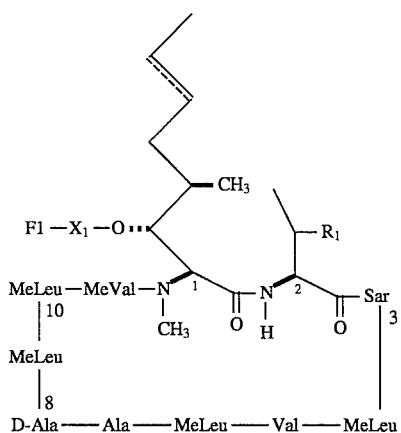

where the symbol

represents a single or a double bond; Fl is a fluorescent moiety; $X_1$ is a linking group of 1–15 atoms, excluding hydrogen; $R_1$ is hydrogen, OH or $OCOR_6$; and $R_6$ is an alkyl group of from 1–6 carbon atoms or $X_1$–Fl; and

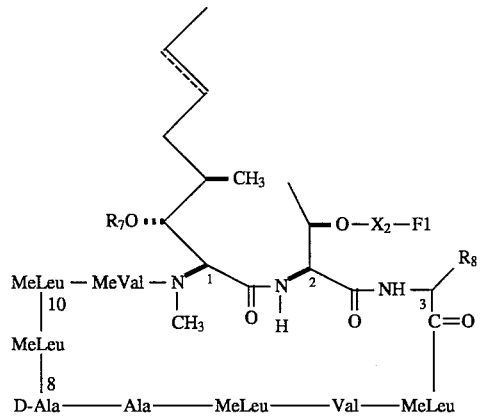

where the symbol

represents a single or a double bond; $R_7$ is hydrogen or an acyl group of 1–6 carbon atoms; $R_8$ is hydrogen or $CH_2OR_7$; $X_2$ is a linking group of 1–30 atoms, excluding hydrogen, and Fl is a fluorescent moiety; and

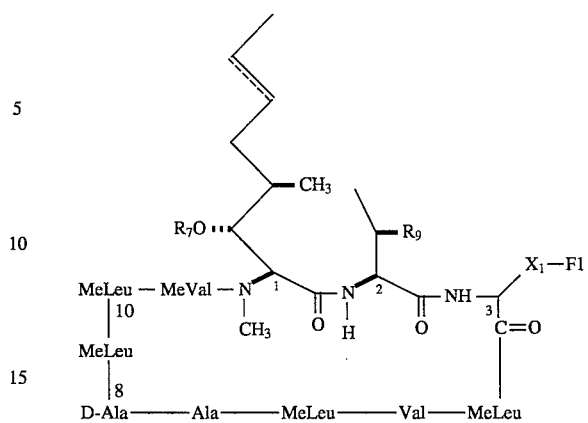

where the symbol

represents a single or double bond; $R_7$ is hydrogen or an acyl group of 1–6 carbon atoms; $R_9$ is hydrogen or $OR_7$; $X_1$ is a linking group of 1–15 atoms, excluding hydrogen; and Fl is a fluorescent moiety; and

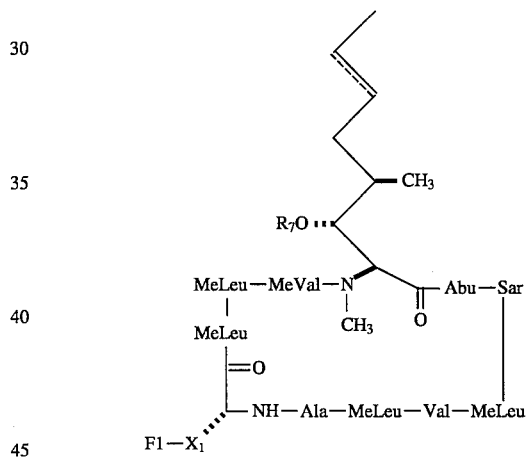

where the symbol

represents a single or double bond; $R_7$ is hydrogen or an acyl group of 1–6 carbon atoms; $X_1$ is a linking group of 1–15 atoms, excluding hydrogen; and Fl is a fluorescent moiety; and

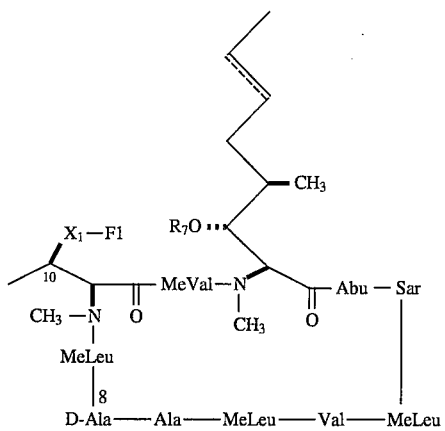

where the symbol

represents a single or a double bond; $R_7$ is hydrogen or an acyl group of 1–6 carbon atoms; $X_1$ is a linking group of 1–15 atoms, excluding hydrogen; and Fl is a fluorescent moiety.

The present invention also provides a method and test kit employing such cyclosporine tracer compounds.

DETAILED DESCRIPTION OF THE INVENTION

The cyclosporine tracer compounds of the present invention are prepared according to the general reaction schemes set forth in FIGS. 1A–1E, wherein R is a cyclosporine moiety, X is a linking group from between 1 and 6 atoms, excluding hydrogen, Y is Cl or $OCH_3$, Z is a detectable moiety, and R' and R" are alkyl groups or functionalized alkyl groups as are commonly found in carbodiimides.

Figure 1A:
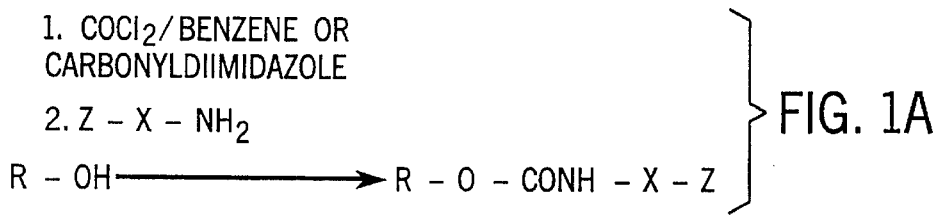
FIGS. 1A–1E illustrate general synthetic pathways for preparing cyclosporine tracer compounds according to the present invention.

For example, according to reaction scheme of FIG. 1A, cyclosporine or derivative thereof containing a free hydroxyl group is treated with a solution of phosgene in benzene or toluene to form an intermediate choroformate. Alternatively, a similar intermediate can be formed using carbonyldiimidazole. The chloroformate is then reacted with, for example, a fluorescein moiety which is substituted with an amino group to form a carbamate linkage, as described in greater detail in examples 3, 4, 5, 13, 14, 16, 17, 18 and 19 hereunder.

Figure 1B:
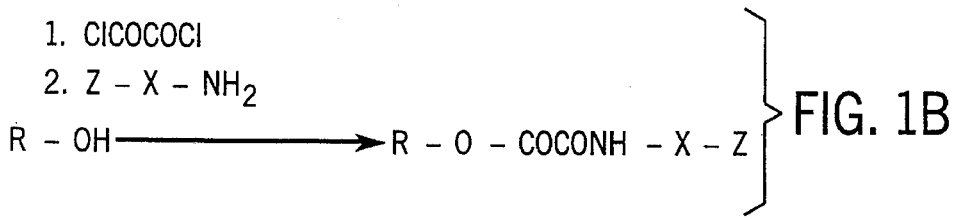

According to reaction scheme FIG. 1B, cyclosporine or a derivative thereof containing a free hydroxyl group is treated with oxalyl chloride to form the intermediate chlorooxalyl ester. This intermediate is then treated with, for example, a fluorescein moiety which is substituted with an amino group to form an amide linkage, as described in greater detail in examples 1 and 2 hereunder.

Figure 1C:
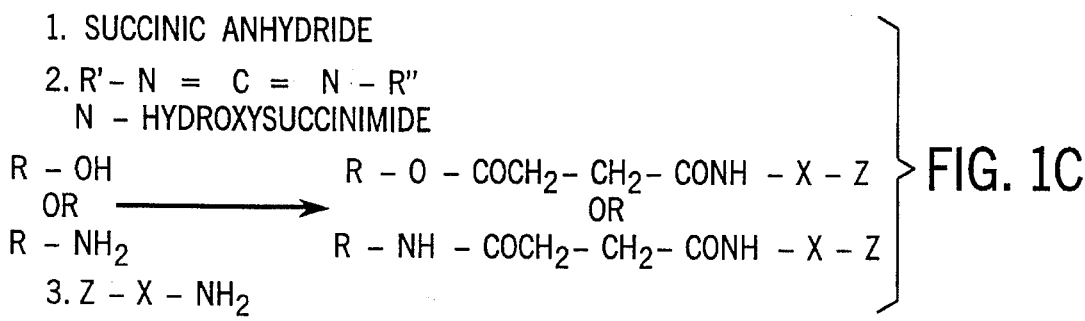

According to reaction scheme of FIG. 1C, cyclosporine or a derivative thereof containing a free hydroxyl group or a free amino group is treated with succinic anhydride to form the intermediate acid half-ester or acid half-amide. The free carboxylic acid thus formed is then activated employing carbodiimide, and subsequently treated with, for example, a fluorescein moiety substituted with an amino group, to form an amide linkage, and, alternatively, may proceed through the intermediacy of an active ester, such as an N-hydroxysuccinimide active ester, as described in greater detail in examples 11, 20, 21, 22, 24, 25, 28, 29, 33, 34, 36, 38, 40 and 43 hereunder.

Figure 1D:
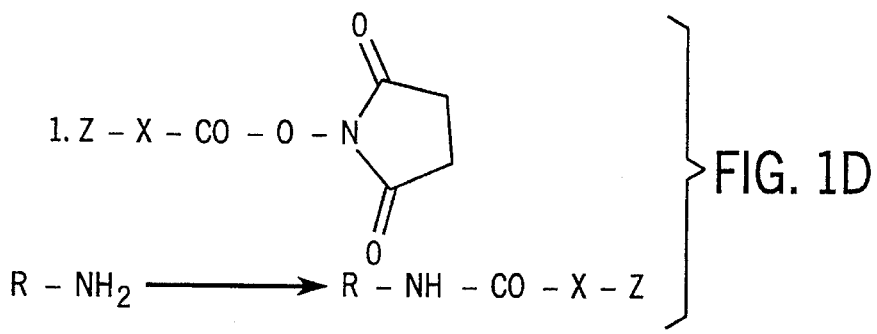

According to reaction scheme of FIG. 1D, cyclosporine or a derivative thereof containing a free amino group is treated with a carboxyfluorescein active ester in the presence of a base. The cyclosporine derivative and the fluorescein moiety are thus linked through an amide bond, as described in greater detail in examples 11, 12, 26 and 32 hereunder.

Figure 1E:
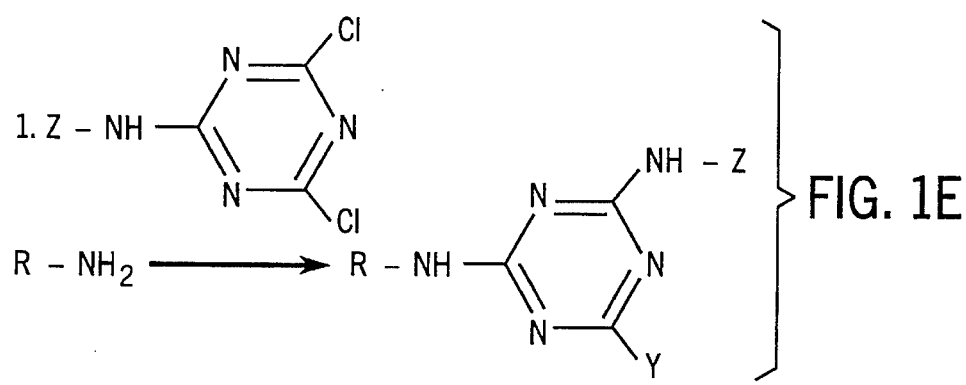

According to reaction scheme of FIG. 1E, cyclosporine or a derivative thereof containing a free amino group is treated with a fluorescein moiety substituted with a dichlorotriazinyl group to form a nitrogen-carbon bond linkage, as described in greater detail in examples 9, 10, 23 and 27 hereunder.

The detectable moiety component of the cyclosporine tracer compounds of the present invention can be selected from a variety of detectable labels known in the art including, but not intended to be limited to, chemiluminescent molecules, luminescent molecules, enzymes, and the like. According to the present invention, luminescent molecules known as fluorescein, and fluorescein derivatives, are preferred. Such fluorescein derivatives include, but are not intended to be limited to, fluoresceinamine, carboxyfluorescein, alpha-iodoacetamidofluorescein, 4'-aminomethylfluorescein, 4'-N-alkylaminomethylfluorescein, 5-aminomethylfluorescein, 6-aminomethylfluorescein, 2,4-dichloro-1,3, 5-triazin-2-yl-aminofluorescein (DTAF), 4-chloro-6-methoxy-1,3,5-triazln-2-yl-aminofluorescein, and fluoresceinisothiocyanate. Particularly preferred derivatives are the aminomethylfluoresceins, the carboxyfluoresceins, and the fluoresceinamines.

Fluorescein exists in two tautomeric forms, depending on the acid concentration (pH) of the environment. In the open (acid) form, fluorescein or a fluorescein derivative (or a tracer containing a fluorescent molecule) is capable of absorbing blue light and emitting green fluorescence after an excited state lifetime of about four nanoseconds. When the open and closed forms coexist, relative concentration of molecules in the open and closed forms is easily altered by adjustment of the pH level. Generally, the cyclosporine tracer compounds of the present invention are prepared in solution as biologically acceptable salts such as sodium, potassium, ammonium and the like, which allows the compounds to exist in the fluorescent form. The specific salt present will depend on the buffer used to adjust the pH level. For example, in the presence of sodium phosphate buffer, the compounds of the present invention will generally exist in the open form, as a sodium salt. Accordingly, the term "fluorescein" as used herein, either as an individual compound or as a component of a tracer, is meant to include both the open and closed tautomeric forms, if they exist for a particular molecule, except in the context of fluorescence, in which case an open form is necessary for the fluorescence to occur. As would be understood by one skilled in the art, fluorescent labels are ideally chosen in accordance with their size, that is, the smaller the molecule, the more rapidly it will be able to rotate, and thus the more effective it will be as a fluorescence polarization immunoassay tracer compound. Such compounds provide fluorescent response when excited by polarized light of an appropriate wavelength and thereby enable the fluorescence polarization measurement.

The cyclosporine tracer compounds according to the present invention can be used to determine the presence or amount of cyclosporine, or metabolites of cyclosporine, in diluted or undiluted test samples such as whole blood, serum, plasma, spinal fluid, and the like, employing conventional immunoassay techniques known in the art. According to the method of the present invention, a test sample suspected of containing cyclosporine, or cyclosporine and metabolites of cyclosporine, is combined with a cyclosporine tracer compound of the present invention and an appropriate antibody thereto prepared according to methods known in the art. Cyclosporine present in the test sample and the tracer compound compete for a limited number of binding sites on the antibody, resulting in the formation of cyclosporine-antibody and tracer compound-antibody complexes. By maintaining a constant concentration of the tracer compound and the antibody, the ratio of the formation of cyclosporine-antibody complex to tracer-antibody complex is directly proportional to the amount of cyclosporine in the test sample.

It is to be understood that the tracer compound of the present invention can be employed in immunoassay systems employing antibodies which recognize cyclosporine, or antibodies which recognize cyclosporine and metabolites of cyclosporine. Monoclonal and polyclonal antibodies to cyclosporine have been described [Donatsch, et al., supra; Quesniaux, et al., supra, and Quesniaux, et al., *International Journal of Peptide and Protein Research*, Vol. 31, pages 173–185 (1988); European Patent Application Publication No. 283,801; Cacalano, et al., *Journal of Immunological Methods*, Vol. 118(2), pages 257–263 (1989); and International Patent Application Publication No. WO 86/02080]. Accordingly, reference to the determination of cyclosporine as described herein is intended to include the specific determination of cyclosporine, independent from any metabolites which may be present in a test sample, or to the determination of cyclosporine and metabolites thereof, which determination will of course depend upon the particular antibody employed in the immunoassay system, as described above.

As would be understood by one skilled in the art, the specificity of an antibody is determined, in part, by the structure of the immunogen used to raise the antibody. Immunogens for small molecular weight analytes are prepared according to methods known in the art by coupling the analyte to a large molecular weight carrier, such as a protein, through a covalent bond in order to ensure an adequate immune response in the laboratory animal. The position of attachment of the carrier to the analyte is such that recognition of the antibody for that site is generally low.

When preparing the tracer compound of the present invention, the position of attachment of the detectable moiety to the derivatized cyclosporine molecule, and the length and character of the linker arm that joins them, should be optimized such that there is a competition between the tracer compound and cyclosporine from the test sample for binding to the antibody. In many instances, it is advantageous to attach the detectable moiety to a site on the cyclosporine molecule that is not well recognized by the antibody, so that the antibody will nevertheless bind to the tracer compound. Typically, there may be sites other than the immunogen attachment site that are poorly recognized by the antibody. Accordingly, changing the length of the linker arm and the character of the linker arm will often optimize the binding of antibody to the tracer compound to achieve the desired results. Furthermore, to be useful for the monitoring of cyclosporine, the competition between analyte and the tracer compound must be such that therapeutic range levels can be distinguished from one another.

The structure of the tracer compound is important to the performance of an immunoassay, and should be optimized for use with the antibody employed in the particular assay. For example, if the antibody binds to the tracer compound with a high affinity, the tracer compound may not be displaced from the antibody by the analyte, or the tracer compound competetively displaces all of the analyte from the antibody, wherein measurement of the analyte cannot be accomplished. Conversely, if the antibody does not recognize the tracer compound, no signal other than any background signal can be detected and no measurement of analyte can be accomplished. Similarly, the structure of the tracer compound determines, to some degree, the cross-reactivity of the antibody to metabolites or analogs of the analyte, since the relative binding properties of antibody with the analyte, analogs of the analyte, and the tracer compound determines the cross-reactivity.

The cyclosporine tracer compounds of the present invention are preferably employed in fluorescence polarization immunoassay systems wherein the amount of cyclosporine in the test sample is determined by exciting the mixture with polarized light and measuring the polarization of the fluorescence emitted by any of the free or unbound tracer compound and tracer-antibody complex. Any of the tracer compound which is not complexed to an antibody is free to rotate in less than the time required for adsorption and re-emission of fluorescent light. As a result, the re-emitted light is relatively randomly oriented so that the fluorescence polarization of any of the tracer compound not complexed to the antibody is low, approaching zero. Upon complexing with a specific antibody, the tracer-antibody complex thus formed assumes the rotation of the antibody molecule, which is slower than that of the relatively small tracer compound molecule, thereby increasing the polarization observed. When making such determination, cyclosporine competes with the tracer compound for antibody sites wherein the observed polarization of fluorescence of the tracer-antibody complex becomes a value between the value of the free tracer compound and the value tracer-antibody complex. Accordingly, if the test sample contains a high concentration of cyclosporine or metabolites thereof, the observed polarization value is closer to that of the free tracer compound, i.e., low. Conversely, if the test sample contains a low concentration of cyclosporine or metabolites thereof, the polarization value is closer to that of the tracer-antibody complex, i.e., high. By sequentially exciting the reaction mixture of an immunoassay with vertically and then horizontally polarized light, and analyzing only the vertical component of the emitted light, the polarization of the fluorescence in the reaction mixture can be accurately determined. The precise relationship between polarization and concentration of cyclosporine is established by measuring the polarization values of calibrators having known concentrations, and the concentration of cyclosporine can be interpolated from a standard curve prepared therefrom.

When employing fluorescence polarization techniques, the results can be quantified in terms of "millipolarization units", "span" (in millipolarization units) and "relative intensity". The measurement of millipolarization units indicates the maximum polarization when a maximum amount of the tracer compound is bound to the antibody in the absence of any analyte in the test sample. The higher the net millipolarization units, the better the binding of the tracer compound to the antibody. For the purposes of the present invention, a net millipolarization value of at least about 130 is preferred.

The "span" is an indication of the difference between the net millipolarization and the minimum amount of the tracer compound bound to the antibody. A larger span provides for a better numerical analysis of the data. For the purposes of the present invention, a span of at least about 15 millipolarization units is preferred.

The "relative intensity" is a measure of the strength of the fluorescence signal above the background fluorescence. Thus, a higher intensity will give a more accurate measurement. The intensity is determined as the sum of the vertically polarized intensity plus twice the horizontally polarized intensity. The intensity can range from a signal of about three times to about thirty times the background noise, depending upon the concentration of the tracer compound and other assay variables. For the purpose of the present invention, an intensity of about three to about twenty times that of background noise is preferred.

When performing an immunoassay method employing a tracer comound according to the present invention, the pH can be from between about 4.0 to about 9.0, preferably from between about 6.0 and 8.0, most preferably from between about 7.0 and 7.5. Where the detecatble moiety of the tracer compound is a fluorescein moiety, the pH of the immunoassay system in which such tracer compound is employed must be sufficient to allow the fluorescein moiety of the tracer compound to exist in the open form. Various buffers can be used to achieve and maintain the pH during an immunoassay procedure and include, but are not intended to be limited to borate, phosphate, carbonate, TRIS™ barbital and the like. Although any of such buffers can be employed, TRIS and phosphate buffers are preferred when performing a fluorescent polarization immunoassay.

The method according to the present invention is carried out at moderate temperatures, preferably at a constant temperature. The temperature will normally be from between about 0° C. to about 50° C., preferably from about 15° C. to about 40° C.

As will be described in greater detail hereinafter, the cyclosporine tracer compounds of the present invention have been found to be particularly useful in a fluoresence polarization immunoassay wherein from between about $10^{-6}M$ to about $10^{-10}M$ of cyclosporine in a test sample can be determined. As would be understood by one skilled in the art, higher concentrations of cyclosporine can be determined by diluting the test sample. Although the concentration range of cyclosporine in a test sample will determine the range of concentration of the assay reagents such as the tracer compound and the antibody, the respective reagent concentrations can be determined empirically to optimize the sensitivity of the assay, as can be determined by one of ordinary skill in the art.

According to a preferred embodiment of the present invention, the reagents for performing a fluorescent polarization immunoassay include a fluorescent tracer compound comprising 4-aminomethylfluorescein coupled to the hydroxyl group of MeBmt at the first position of cyclosporine, as described in Example 4 hereunder and represented by the formula

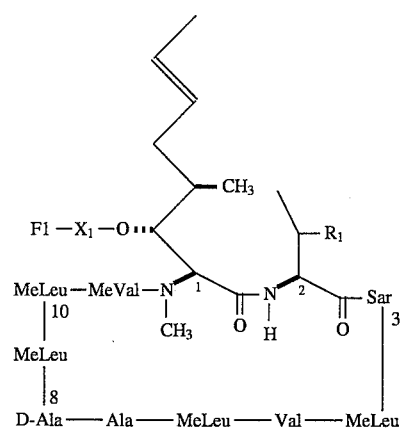

where $R_1$ is hydrogen, $X_1$ is a

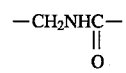

moiety, and Fl is fluorescein coupled at the 4' position thereof, and a monoclonal antibody to cyclosporine, such as described by International Patent Application Publication No. WO 86/02080. The use of such fluorescent tracer compound of the formula was found to be surprisingly useful with such monoclonal antibody since such antibody was prepared with an immunogen coupled to a carrier protein molecule through the amino acid at the second position of cyclosporine, wherein the binding properties of a cyclosporine antibody are otherwise particularly sensitive to structural changes at the first position. As will described in greater detail in the Examples hereunder, a cyclosporine monoclonal whole blood precipitation solution comprising methanol, ethylene glycol and zinc sulfate as described in the application Ser. No. 07/567,853, entitled Protein Precipitation Reagent, Aug. 15, 1990, now U.S. Pat. No. 5,135,875, issued Aug. 4, 1992 and incorporated by reference herein, and a solubilization reagent comprising saponin and a detergent such as TERGITOL™ [alkyloxy(polyethyleneoxy propyleneoxyisoproponol], such as described in the copending U.S. patent application (Ser. No. 07/567,840), entitled "Solubilization Reagent For Biological Test Samples", filed on Aug. 15, 1990, now abandoned and incorporated by reference herein, are also employed. In addition, a dilution buffer, calibrators and controls are preferably employed.

A preferred immunoassay procedure according to the present invention is a homogeneous immunoassay wherein the fluorescence polarization readings are taken from a solution containing antibody-fluorescent tracer compound complexes and free or unbound fluorescent tracer compounds, and therefore not requiring separation of such species. Such immunoassay procedure is particularly advantageous over, for example, radioimmunoassay procedures where the bound radioactive tracer must be separated from the unbound radioactive tracer before a reading can be taken.

According to the preferred assay procedure of the present invention, the test sample containing cyclosporine, or cyclosporine and metabolites thereof, are combined with the precipitation reagent described above, mixed and centrifuged, wherein a pellet of denatured protein is obtained. It is to be understood that cyclosporine and metabolites of cyclosporine have a particularly high binding affinity for proteins, especially lipoproteins. Accordingly, in order to separate cyclosporine and metabolites of cyclosporine from such proteins which would otherwise interfere with the immunoassay determination of cyclosporine and metabolites thereof as provided herein, the precipitation reagent is employed to accomplish such separation wherein proteins present in a test sample are precipitated while, at the same time, recovering from between about 90% and 110% of the cyclosporine or cyclosporine and cyclosporine metabolites present in the test sample. Similarly, where the test sample is, for example, a whole blood test sample or other biological test sample containing various cellular components, it is desirable to dissociate any cyclosporine or cyclosporine and metabolites thereof from such cellular components in order to render any cyclosporine and metabolites thereof available for binding to the antibody. Accordingly, the solubilization reagent described above is employed to dissociate any cyclosporine or cyclosporine and metabolites thereof from such cellular components of the test sample.

Once the interfering proteins have been precipitated as described above and, in the case of, for example, a whole blood test sample, the sample first treated with the solubilization reagent as described above, the supernatant containing cyclosporine, or cyclosporine and metabolites of cyclosporine, is then combined with the antibody. Prior to addition of the tracer compound and dilution buffer, a background fluorescence reading is taken, wherein after an incubation period of from between about ten minutes and about thirty minutes, a fluorescence polarization reading is taken as described above.

A test kit according to the present invention comprises all of the essential reagents required to perform a desired immunoassay according to the present invention. The test kit is presented in a commercially packaged form as a combination of one or more containers holding the necessary reagents, as a composition or admixture where the compatibility of the reagents will allow. Particularly preferred is a test kit for the fluorescent polarization immunoassay determination of cyclosporine, or cyclosporine and metabolites of cyclosporine, comprising an appropriate fluorescent tracer compound of the present invention, an appropriate antibody reagent, a precipitation reagent and, where the test sample is a whole blood test sample, a solubilization reagent as described above. It is to be understood that the test kit can, of course, include other materials as are known in the art and which may be desirable from a commercial user standpoint, such as buffers, diluents, standards, and the like.

The present invention will now be illustrated, but is not intended to be limited, by the following examples:

EXAMPLE 1

[O-(Chlorooxalyl)MeBmt]$^1$cyclosporine

Cyclosporine (34.3 mg, 0.0285 mmoles) and dimethylaminopyridine (30.2 mg, 0.247 mmoles) were dissolved in oxalyl chloride (1.0 mL) at 0° C. The flask was fitted with a stirbar and a drying tube, and the reaction was stirred on an ice bath for 3.5 hours. The reaction was concentrated to dryness in vacuo. The residue was taken up into 1.0 mL of dry dimethylformamide to make a 0.03 M solution, and used in subsequent reactions.

EXAMPLE 2

[O-(Fluorescein-5-ylaminooxalyl)MeBmt]$^1$cyclosporine

The DMF solution described in Example 1 (0.33 mL, 9.5 μmoles) was combined with fluoresceinamine isomer I (5.2 mg, 15 μmoles) in a stoppered flask fitted with a stirbar. Pyridine was added until the apparent pH (determined by spotting the solution on moist pH paper) was approximately 4–5. The reaction stirred at room temperature for 3 days. The solvent was removed in vacuo and the residue taken up in 0.5 mL of methanol and applied to a 0.5 mm silica gel plate (20×20 cm). The plate was developed in 15% methanol/methylene chloride. The fluorescent band at Rf 0.5 was removed from the silica gel with methanol and repurified on a 0.5 mm silica gel plate (20×20 cm), eluting twice with 5% methanol/methylene chloride. The desired band (Rf 0.37) was removed from the silica gel with methanol.

EXAMPLE 3

[O-(Chloroformyl)MeBmt]$^1$cyclosporine (Cyclosporine chloroformate)

Cyclosporine (24.2 mg, 0.020 mmoles) was dissolved in a 25 %w/w solution of phosgene in benzene (2.0 mL) in a 10 mL round bottom flask fitted with stopper and stirbar. The reaction was stirred for 5 minutes to dissolve the cyclosporine, then was allowed to stand undisturbed at room temperature for 24 hours. The reaction was concentrated in vacuo, and the product could be stored as a solid at 0° C. for up to six months. For subsequent reactions, a 0.02 M solution in DMF was used.

EXAMPLE 4

[O-(Fluorescein-4'-ylmethylaminoformyl)MeBmt]$^1$cyclosporine

Cyclosporine chloroformate, as a 0.02M solution in DMF as described in Example 3 (0.2 mL, 4 μmoles) was combined with 4'-aminomethylfluorescein hydrochloride (2.0 mg, 5 moles) in a stoppered vial fitted with a stirbar. Pyridine was added until the apparent pH (by moist pH paper) was approximately 7. The reaction was stirred at room temperature for 24 hours. The solvent was removed in vacuo, and the residue was taken up in methanol and loaded onto a 1 mm silica gel plate. The plate was developed with 15% methanol/methylene chloride. The product band, Rf 0.55, was eluted from the silica gel with methanol.

EXAMPLE 5

[O-(Fluorescein-5-ylmethylaminoformyl)MeBmt]$^1$cyclosporine

Cyclosporine chloroformate (5 mg of the solid described in Example 3, 4.0 umole) was dissolved in 150 uL of dry DMF in a stoppered vial fitted with a stirbar. 5-Aminomethylfluorescein hydrochloride (3.2mg, 8 umole) and triethylamine (2.2uL, 16 umole) were added, and the reaction stirred at room temperature for 2.5 days. The solvent was removed in vacuo, and the residue was taken up in methanol and applied to a 1 mm silica gel plate, which was eluted with 15% methanol/methylene chloride. The fluorescent band at Rf 0.64 was isolated and removed from the silica gel with methanol.

EXAMPLE 6

[O-(Chloroacetyl)MeBmt]$^1$cyclosporine

Cyclosporine (1.01g, 0.840 mmoles) was dissolved in chloroacetyl chloride (3.0 mL) in a round bottom flask fitted with stirbar and drying tube. Dimethylaminopyridine (152.4 mg, 1.25 mmoles) was added. The reaction was stirred at room temperature for 2.5 days. The reaction solution was poured into 10 mL of cold (0°) saturated NaHCO$_3$ and stirred, while solid NaHCO$_3$ was added portionwise until bubbling ceased, about 2 hours. The solution was extracted with 3×20 mL of diethyl ether. The combined ethereal extracts were washed with 1×10 mL of 0.1N HCl, 3×10 mL of water, and 1×10 mL of saturated NaCl solution. The organic layer was dried over anhydrous $MgSO_4$, filtered, and concentrated in vacuo to give 1.02 g of a yellow glassy residue. This material was subjected to flash chromatography on 75 g of silica gel using 5% methanol/methylene chloride as eluent. Fractions containing product were combined and concentrated to give 0.52 g of the title compound (48% yield). Fast-atom bombardment mass spectrometry showed and (M+H) signal at 1278.

EXAMPLE 7

[O-(Azidoacetyl)MeBmt]$^1$cyclosporine

[O-(Chloroacetyl)MeBmt]$^1$ cyclosporine (103.3 mg, 0.0808 mmoles) and sodium azide (6.5 mg, 0.10 mmoles) were combined in a round bottom flask fitted with stirbar and reflux condenser. Dimethylformamide (1.0 mL) and 1 drop of water (to dissolve the sodium azide) were added. The reaction was stirred at 50° C. overnight, then 90° C. for 1.5 hours. The solution was taken up into 20mL of ether and washed with 3×10 mL of water and 1×5 mL of saturated NaCl solution, dried over $MgSO^4$, filtered and concentrated in vacuo to give 92.1 mg (88%) of a slightly yellow solid. TLC (silica gel, 5% methanol/methylene chloride) showed minor impurities. IR showed azide absorption at 2100 cm-1.

EXAMPLE 8

[O-(Glycyl)MeBmt]$^1$cyclosporine

[O-(Azidoacetyl)MeBmt]$^1$cyclosporine (46.1 mg, 0.0359 mmoles) was dissolved in 5.0 mL of absolute ethanol in a 100 mL Parr hydrogenation bottle. 5% Palladium on calcium carbonate, poisoned with lead (36.1 mg, 78%w/w), and triethylamine (100 uL) were added, and the reaction was shaken on a Parr apparatus at 50 psi H2 at room temperature overnight. The reaction was removed from the apparatus and filtered through a pad of CELITE. The CELITE was washed with additional ethanol. The combined filtrate and washings were concentrated in vacuo to give 42 mg of a mixture of two components by TLC (silica gel, 5% methanol/methylene chloride, Rf's 0.3 and 0.18). The mixture was separated on a CHROMATORON (Harrison Research, 810 Moana Court, Palo Alto, Calif.) using a 1 mm rotor and eluting with 5% methanol/methylene chloride. Fractions containing pure product were combined to give 23.4 mg of O-(glycyl)cyclosporine, 52 % yield. FAB MS showed (M+H)+1259 and (M+Na)+1271 for the desired compound.

EXAMPLE 9

[O-(5-Fluorescein-5-ylamino-3-chlorotriazinylglycyl)MeBmt]$^1$cyclosporine

[O-(Gycyl)MeBmt]$^1$cyclosporine (Example 8, 5 mg, 4 umole) was dissolved in 8 uL of methanol in a stoppered vial equipped with a stirbar. 3,5-Dichlorotriazinylaminofluorescein isomer I (DTAF-I, 4.0 mg, 8 umole) was added, and the reaction was stirred at room temperature for 3.5 days. The solution was loaded onto a 1 mm silica gel plate and developed with 20% methanol/methylene chloride. The band at Rf 0.75 was eluted from the silica gel with methanol and repurified on a 1 mm silica gel plate, developing with 5% methanol/methylene chloride. The band at Rf 0.3 was eluted from the silica gel with methanol.

EXAMPLE 10

[O-(5-Fluorescein-6-ylamino-3-chlorotriazinylglycyl)MeBmt]$^1$cyclosporine

The procedure in Example 9 was followed, using dichlorotriazinylaminofluorescein isomer II (DTAF-II) in the place of DTAF-I. The reaction was Stirred for 1 day. The first purification was done with 20% methanol/methylene chloride (Rf 0.70) and the second purification was done with 10% methanol/methylene chloride (Rf 0.71).

EXAMPLE 11

[O-(Fluorescein-5-carboxylglycyl)MeBmt]$^1$cyclosporine

[O-(Glycyl)MeBmt]$^1$cyclosporine (Example 8, 5 mg, 4 umole) and the N-hydroxysuccinimide ester of 5-carboxyfluorescein (3.0 mg, 8 umole) were combined in a stoppered vial fitted with a stirbar, with dimethylformamide (50 uL), triethylamine (3.3 uL, 24 umole), and dimethylaminopyridine (5 umole). The reaction was stirred at room temperature overnight. The volatiles were removed in vacuo, and the residue was taken up in methanol and loaded onto a 1 mm silica gel plate. The plate was developed with 20% methanol/methylene chloride, and the band at Rf 0.64 was removed from the silica gel with methanol. Repurification by preparative thin layer chromatography with 2×10% methanol/methylene chloride gave a single band, Rf 0.43.

EXAMPLE 12

[O-(Fluorescein-6-carboxylglycyl)MeBmt]$^1$cyclosporine

The procedure in Example 11 was followed using the N-hydroxysuccinimide ester of 6-carboxyfluorescein. The Rf of the desired band after 1 development with 20% methanol/methylene chloride was 0.65; after the second purification with 2×10% methanol/methylene chloride the Rf was 0.4.

EXAMPLE 13

[O-(N-fluorescein-4'-ylmethyl acetamidoaminoformyl)MeBmt]$^1$cyclosporine

Cyclosporine chloroformate, as a solution in DMF (Example 3, 4 moles) was combined with 4'-N-glycylaminomethylfluorescein hydrochloride (2.4 mg, 5.3 μmoles) in a stoppered vial fitted with a stirbar. Pyridine (approx. 10 drops) was added until the apparent pH was about 8. The reaction was stirred at room temperature for 1 day. The volatiles were removed in vacuo and the residue was taken up into methanol and loaded onto a 1 mm silica gel plate. The plate was eluted with 15% methanol/methylene chloride. The band at Rf 0.5 was eluted from the silica gel with methanol. Repurification using 20% methanol/methylene chloride gave a band at Rf 0.6.

EXAMPLE 14

[O-(Fluorescein-5-ylaminoformyl)MeBmt]$^1$cyclosporine

Cyclosporine chloroformate, as a solution in DMF (Example 3, 4 moles) was combined with fluoresceinamine isomer I (6.2 mg, 18 μmoles) in a stoppered vial fitted with a stirbar. Pyridine was added until the apparent pH was about 7. The reaction was stirred at room temperature for 1 day. The volatiles were removed in vacuo and the residue was taken up into methanol and loaded onto a 1 mm silica gel plate. The plate was eluted with 15% methanol/methylene chloride. The band at Rf 0.57 was eluted from the silica gel with methanol. Repurification using 10% methanol/methylene chloride gave a band at Rf 0.5.

EXAMPLE 15

[O-AcetylThr]$^2$cyclosporine

[Thr]$^2$cyclosporine (cyclosporin C, obtained from Sandoz AG, Basle, Switzerland; 0.30 g, 0.25 mmole) was dissolved in dry pyridine (1.0 mL) in a round bottom flask fitted with stirbar and drying tube. The solution was cooled to 0° C. on an ice bath. Acetic anhydride (28 uL, 0.30 mmole) was added, and the ice bath was removed. After stirring at room temperature for 3 hours, more acetic anyhydride (28 uL, 0.60 mmoles total) was added. The reaction was stirred at room temperature overnight, and another 10 uL of acetic anhydride was added (total 0.7 mmole). After another 6 hours stirring at room temperature, the reaction was taken up into 25 mL of ether and washed with 1.2N HCl (25 mL), water (25 mL) and saturated NaCl solution (25 mL). The organic layer was dried over anhydrous $MgSO_4$, filtered and concentrated in vacuo. The residue was taken up in $CH_2Cl_2$ and cyclohexane to remove traces of acetic acid. The title compound was obtained in 82% yield (259 mg). Structure of the product was confirmed by 200MHz NMR, which revealed the disappearance of a triplet at delta 4.15 and appearance of a doublet at delta 5.6 and a singlet at delta 1.9.

EXAMPLE 16

[O-ChlorocarbonylMeBmt]$^1$[O-acetylThr]$^2$cyclosporine

[O-AcetylThr]$^2$cyclosporine (Example 15, 17.3 mg, 13.7 mole) was dissolved in a 25% w/w solution of phosgene in benzene (1.0 mL) in a round bottom flask fitted with a tight stopper and stirbar. After stirring for 5 minutes to completely dissolve the peptide, the reaction stood at room temperature overnight. The volatiles were removed in vacuo to leave an off-white solid residue.

EXAMPLE 17

[O-(Fluorescein-4'-ylmethylaminoformyl)MeBmt]$^1$[O-acetylThr]$^2$cyclosporine

[O-ChlorocarbonylMeBmt]$^1$[O-acetylThr]$^2$cyclosporine (Example 16, 4.6 μmoles) in 0.3 mL of dry pyridine, was combined with 4'-aminomethylfluorescein hydrochloride (5.5 mg, 13.8 μmoles) in a stoppered vial fitted with a stirbar. The reaction was stirred at room temperature for 3 days. The solvent was removed in vacuo, and the residue was taken up in methanol and loaded onto a 1 mm silica gel plate. The plate was developed with 15% methanol/methylene chloride. The product band, Rf 0.95, was eluted from the silica gel with methanol. Repurification using 2×5% methanol/methylene chloride gave the product as a single band at Rf 0.4. The band was removed from the silica gel with methanol.

EXAMPLE 18

[O-(Imidazol-1-ylcarbonyl)Thr]$^2$cyclosporine

[Thr]$^2$cyclosporine (14.6 mg, 12.0 moles) was placed in a round bottom flask fitted with stirbar and drying tube. Carbonyldiimidazole (14.8 μmoles), dimethylaminopyridine (14.5 μmoles), dimethylformamide (44 μL) and methylene chloride (120 μL) were added. The reaction was stirred at room temperature for 24 hours. The volatiles were removed, and the residue was carried on immediately to subsequent reactions.

EXAMPLE 19

[O-(Fluorescein-4'-ylmethylaminocarbonyl)Thr]$^2$cyclosporine

[O-(Imidazol-1-ylcarbonyl)Thr]$^2$cyclosporine (Example 18, 6 moles) and 4'-aminomethylfluorescein hydrochloride (5.2 mg, 13 moles) were combined in 100 L of dry dimethylformamide in a stoppered vial fitted with a stirbar. 4-Methylmorpholine (3 μL, 27 moles) was added, and the reaction was stirred at room temperature overnight. The volatiles were removed and the residue was taken up into methanol. The solution was purified on two 0.5 mm silica gel plates, which were eluted with 15% methanol/methylene chloride. The bands at Rf 0.9 were eluted from the silica gel with methanol to isolate the title compound.

EXAMPLE 20

[O-(N-(N-(Fluorescein-4'-ylmethyl)carboxamidomethyl) carboxamidomethyl)Thr]$^2$cyclosporine (a) [O-(Succinimid-N-yloxycarbonylmethyl)Thr]$^2$cyclosporine

[O-(Carboxymethyl)Thr]$^2$cyclosporine (obtained from Sandoz AG, Basle, Switzerland; 20.3 mg, 15.9 μmoles) and N-hydroxysuccinimide (7.8 mg, 67.8 μmoles) were dissolved in dry dimethylformamide (400 μL) in a round bottom flask fitted with a stirbar and drying tube. 1-Ethyl-1'-[(3'-dimethylamino)propyl]carbodiimide hydrochloride (9.2 mg, 48 μmoles) was added, and the reaction was stirred at room temperature overnight. The reaction solution was used in subsequent reactions without purification.

(b) [O-(N-(N-(Fluorescein-4'-ylmethy)carboxamidomethyl) carboxamidomethyl)Thr]$^2$cyclosporine

[O-(Succinimid-N-yloxycarbonylmethyl)Thr]$^2$cyclosporine (as a reaction solution, Example 20, part (a), 4 μmoles) and N-glycyl-4'-aminomethylfluorescein hydrochloride (6.2 μmoles) were combined in a stoppered vial equipped with a stirbar. 4-Methylmorpholine (2.0 L, 18.2 μmoles) was added. The reaction stirred at room temperature overnight. The volatiles were removed under high vacuum. The residue was taken up into methanol and applied to a 0.5 mm silica gel plate, which was eluted with 15% methanol/methylene chloride. The band at Rf 0.9 was eluted from the silica gel with methanol and repurified, eluting with 5% methanol/methylene chloride. The band at Rf 0.45 was removed from the silica gel with methanol.

EXAMPLE 21

[O-(N-(Fluorescein-4'-ylmethyl)carboxamidomethyl)Thr]$^2$cyclosporine

[O-(Succinimid-N-yloxycarbonylmethyl)Thr]$^2$cyclosporine (as a reaction solution, Example 20, 4 μmoles) and 4'-aminomethylfluorescein hydrochloride (3.1 mg, 7.8 moles) were combined in a stoppered vial fitted with a stirbar. 4-Methylmorpholine (2.0 L, 18.2 moles) was added. The reaction stirred at room temperature overnight. The volatiles were removed under high vacuum. The residue was taken up into methanol and applied to a 0.5 mm silica gel plate, which was eluted with 15% methanol/methylene chloride. The band at Rf 0.8 was eluted from the silica gel with methanol and repurified in the same manner, eluting 5% methanol/methylene chloride. The band at Rf 0.55 was removed from the silica gel with methanol.

EXAMPLE 22

[O-(N-methyl-N-(fluorescein-4-ylmethyl)carboxamidomethyl)Thr]$^2$cyclosporine

[O-(Succinimid-N-yloxycarbonylmethyl)Thr]$^2$cyclosporine (as a reaction solution, Example 20, 4 μmoles) and 4'-methylaminomethylfluorescein hydrochloride (2.8 mg, 6.8 μmoles) were combined in a stoppered vial fitted with a stirbar. 4-Methylmorpholine (2.0 L, 18.2 μmoles) was added. The reaction stirred at room temperature overnight. The volatiles were removed under high vacuum. The residue was taken up into methanol and applied to a 0.5 mm silica gel plate, which was eluted with 15% methanol/methylene chloride. The band at Rf 0.92 was eluted from the silica gel with methanol and repurified in the same manner, eluting with 2×5% methanol/methylene chloride. The band at Rf 0.50 was removed from the silica gel with methanol.

EXAMPLE 23

[O-(5-Fluorescein-5-ylamino-3-chlorotriazinyl-2-aminoethyl)Thr]$^2$cyclosporine

[O-(2-aminoethyl)Thr]$^2$cyclosporine (obtained from Sandoz AG, Basle, Switzerland; 5 mg, 4 moles) and DTAF-I (4 mg, 8 μmoles) were dissolved in 60 L of methanol in a stoppered vial equipped with a stirbar, and stirred at room temperature overnight. The solution was applied to a 0.5 mm silica gel plate and eluted with 20% methanol/methylene chloride. The band at Rf 0.46 was removed from the silica gel with methanol, and repurified in the same manner using 2×5% methanol/methylene chloride. The band at Rf 0.5 was removed from the silica gel with methanol.

EXAMPLE 24

[O-(Fluorescein-4'-ylmethylaminosuccinyl)Thr]$^2$cyclosporine

[O-(Succinimid-N-yloxysuccinyl)Thr]$^2$cyclosporine (obtained from Sandoz AG, Basle, Switzerland; 5 mg, 3.5 μmoles), 4'-aminomethylfluorescein hydrochloride (2.9 mg, 7 μmoles), dimethylaminopyridine (6.5 μmoles), and triethylamine (1 μL, 7 moles)were combined in 65 μL of dry dimethylformamide. The reaction was stirred at room temperature for 2.5 days. The solvent was removed in vacuo, the residue was taken up in methanol and applied to a 1 mm silica gel plate. The plate was eluted with 10% methanol/methylene chloride and the band at Rf 0.8 was eluted from the silica gel with methanol. The band was repurified in the same manner, using 2×5% methanol/methylene chloride and 1×10% methanol/methylene chloride to develop the plate. The band at Rf 0.7 was removed from the silica gel with methanol.

EXAMPLE 25

[O-(N-(Fluorescein-4'-ylmethyl)carboxamidomethylaminosuccinyl)Thr]$^2$cyclosporine

[O-(Succinimidyloxysuccinyl)Thr]$^2$cyclosporine (obtained from Sandoz AG, Basle, Switzerland; 5 mg, 3.5 μmoles), 4'-glycylaminomethylfluorescein hydrochloride (2.9 mg, 7 μmoles), dimethylaminopyridine (3.5 μmoles), and triethylamine (1 L, 7 μmoles)were combined in 100 μL of dry dimethylformamide. The reaction was stirred at room temperature for 2.5 days. The solvent was removed in vacuo, the residue was taken up in methanol and applied to a 1 mm silica gel plate. The plate was eluted with 20% methanol/methylene chloride and the band at Rf 0.85was eluted from the silica gel with methanol. The band was repurified in the same manner, using 1×10% methanol/methylene chloride and 1×20% methanol/methylene chloride to develop the plate. The band at Rf 0.75was removed from the silica gel with methanol.

EXAMPLE 26

[O-(N-(Fluorescein-6-ylcarbonylaminoethyl)aminosuccinyl)Thr]$^2$cyclosporine
(a) [O-(N-(2-BOC-aminoethyl)aminosuccinyl)Thr]$^2$cyclosporine

[O-(Succinimidyloxysuccinyl)Thr]$^2$cyclosporine (15 mg, 10.7 μmoles), mono-BOC-ethylenediamine (4.6 mg, 28.7 μmoles), and dimethylaminopyridine (2 μmoles) were combined in 150 L of dry dimethylformamide. The reaction was stirred at room temperature overnight. The reaction was taken up in 25 mL of ether and washed with 4×10 ml of water and 1×10 mL of saturated NaCl solution. The organic layer was dried over anhydrous sodium sulfate, filtered and concentrated. After subjecting to high vacuum overnight, the residue was purified on a CHROMATOTRON using a 1 mm rotor and eluting with 5%–10% methanol/methylene chloride. Pure fractions were combined and concentrated to give 14.7 mg (10 μmoles, 93% yield) of the title compound. FAB MS shows (M+H)$^+$1460.
(b) [O-(N-(2-Aminoethyl)aminosuccinyl)Thr]$^2$cyclosporine

[O-(N-(2-BOC-aminoethyl)aminosuccinyl)Thr]$^2$cyclosporine (Example 26; 14.7 mg, 10 μmoles) was dissolved in trifluoroacetic acid (300 μL) at 0° C. and stirred at that temperature overnight. The reaction was poured onto 0.5 g of NaHCO$_3$ and 10 g of ice. After bubbling ceased, the solution was extracted with 3×20 mL of methylene chloride. The organic extracts were combined and dried over anhydrous sodium sulfate. Filtration and concentration gave 10.5 mg of product.
(c) [O-(2-Fluorescein-6-ylcarbonylaminoethyl)aminosuccinyl)Thr]$^2$cyclosporine

[O-(N-(2-Aminoethyl)aminosuccinyl)Thr]$^2$cyclosporine and 6-(succinimidooxycarbonyl)fluorescein (Research Organics; 2.3 mg, 4.9 μmoles) were combined in dry dimethylformamide (100 μL) in a stoppered vial equipped with a stirbar. 4-Methylmorpholine (1 drop) was added to give an apparent pH of 7–8. The reaction was stirred at room temperature overnight. The volatiles were removed in vacuo and the residue was taken up in methanol and applied to 2–0.5 mm silica gel plates. The plates were developed with 2×15% methanol/methylene chloride. The band at Rf 0.8 was eluted from the silica gel with methanol to give the title compound.

EXAMPLE 27

[O-(2-(3-Chloro-5-(fluorescein-5-ylamino)triazin-1-yl)aminoethylaminosuccinyl)Thr]$^2$cyclosporine

[O-(N-(2-Aminoethyl)aminosuccinyl)Thr]$^2$cyclosporine (3.5 mg, 2 μmoles) and dichlorotriazinylaminofluorescein isomer I (DTAF-I, 2.5 mg, 5 μmoles) were combined in 100 L of methanol in a stoppered vial fitted with a stirbar. The reaction was stirred at room temperature overnight, then applied to a 0.5 mm silica gel plate and eluted with 2×15% methanol/methylene chloride. The band at Rf 0.5 was removed from the silica gel with methanol to give the title compound.

EXAMPLE 28

[O-(N-(Fluorescein-4'-ylmethyl)-N-methyl-aminosuccinylpoly-(oxyethyl)succinyl)Thr]$^2$cyclosporine
a. [O-(Poly(oxyethyl)succinyl)Thr]$^2$cyclosporine

[O-(Succinyl)Thr]$^2$cyclosporine (350 mg, 0.265 mmole) was dissolved in dry CH$_2$Cl$_2$ (0.5 mL) with polyethylene glycol (avg. MW 200g/mole, 82.2 mg, approx. 0.91 mmole), N-ethyl-N'-dimethylaminopropylcarbodiimide hydrochloride (90.2 mg, 0.471 mmole), and dimethylaminopyridine (46.7 mg, 0.382 mmole), in a round bottom flask fitted with stirbar and drying tube. The reaction stirred at room temperature overnight. The solution was taken up in 20 mL of ether and washed with 2×5 mL of 0.12N HCl, 2×10 mL of water, 2×5 mL of 5% NaHCO$_3$, 3×10 mL of water, and 1×5 mL of saturated NaCl solution. The organic layer was dried over anhydrous Na$_2$SO$_4$, filtered and concentrated to give 299.4 mg of a white foam. The product was purified on a CHROMATOTRON using a 1 mm rotor and eluting with 3% methanol/methylene chloride. Fractions containing pure product were combined and concentrated to give 240.6 mg (60% yield). FAB MS gave four parent peaks, differing in mass by 44: $(M+H)^+$ 1538, 1494, 1450, 1406.

b. [O-(Hydroxysuccinylpoly(oxyethyl)succinyl)Thr]$^2$cyclosporine

[O-(Poly(oxyethyl)succinyl)threonyl]$^2$cyclosporine (Example 28; 83.8 mg, 55.9 μmoles), succinic anhydride (8.9 mg, 89 μmoles), and dimethylaminopyridine (80 moles) were dissolved in DMF (1 mL) in a round bottom flask fitted with stirbar and drying tube. The reaction was stirred at room temperature overnight. The solution was taken up into ether (25 mL) and washed with 5 mL of 0.12N HCl, 3×5 mL of water, and 10 mL of saturated NaCl solution. The organic layer was dried over anhydrous $MgSO_4$, filtered and concentrated to give 67.4 mg (86%) of the title compound.

c. [O-(N-(Fluorescein-4'-ylmethyl)-N-methyl aminosuccinylpoly(oxyethyl)succinyl)Thr]$^2$cyclosporine

[O-(Succinylpoly(oxyethyl)succinyl)Thr]$^2$cyclosporine (Example 28; 5 mg, 3.1 moles), diisopropylcarbodiimide (0.58 L, 3.7 μmoles), N-hydroxybenzotriazole (1.1 mg, 7 μmoles), triethylamine (1.4 L, 10 μmoles),and 4'-methylaminomethylfluorescein (1.4 mg, 3.7 μmoles) were combined in DMF (150 L) in a stoppered vial fitted with a stirbar. The reaction was stirred at room temperature overnight. The volatiles were removed in vacuo, and the residue was taken up in methanol and applied to a 0.5 mm silica gel plate. The plate was eluted with 20% methanol/methylene chloride. The desired compound was removed from the band at Rf 0.8 with methanol.

EXAMPLE 29

[DihydroMeBmt]$^1$[O-(fluorescein-4-ylmethylaminosuccinyl)Thr]$^2$cyclosporine (a) [DihydroMeBmt]$^1$[O-(succinyl)Thr]$^2$cyclosporine Dihydrocyclosporine C was reacted with succinic anhydride according to the procedure to give the title compound.

(b) [DihydroMeBmt]$^1$[O-(N-fluorescein-4'-ylmethylaminosuccinyl)Thr]$^2$cyclosporine.

[DihydroMeBmt]$^1$[O-(succinyl)Thr]$^2$cyclosporine (0.8 mg, 0.6 μmole) was combined with diisopropylcarbodiimide (0.21 L, 1.3 μmoles), N-hydroxybenzotriazole (0.34 mg, 2.2 μmoles), 4'-aminomethylfluorescein hydrochloride (0.54 mg, 1.3 μmoles), and triethylamine (0.45 L, 3.3 μmoles) in DMF (50 L).in a stoppered vial equipped with a stirbar. The reaction was stirred at room temperature overnight. The volatiles were removed in vacuo, and the residue was taken up into methanol and applied to a 0.5 mm silica gel plate. The plate was eluted with 20% methanol/methylene chloride. The band at Rf 0.61 was collected and the compound removed from the silica gel with methanol. Repurification in the same manner using 2×15% methanol/methylene chloride gave the product band at Rf 0.5. The compound was removed from the silica gel with methanol to give the title compound.

EXAMPLE 30

[O-(Fluorescein-4'-ylmethylaminocarbonyl)-(D)-MeSer]$^3$cyclosporine

[(D)-MeSer]$^3$cyclosporine (13.3 mg, 10.8 μmoles), 1,1'-carbonyldiimidazole (13 moles), and dimethylaminopyridine (13 μmoles) were combined in DMF (0.5 mL) in a round bottom flask fitted with stirbar and drying tube. The reaction stirred at room temperature for 24 hours. To one-third of this reaction mixture was added 4'-aminomethylfluorescein hydrochloride(3.6 mg, 9 μmoles ) and 4-methylmorpholine (2.0 L, 18.2 μmoles) . The apparent pH was 8–9 by moist pH paper. The reaction was further stirred at room temperature for 24 hours. The volatiles were removed in vacuo, and the residue was taken up into methanol and applied to a 1 mm silica gel plate. The plate was eluted with 15% methanol/methylene chloride. The band at Rf 0.6 was removed, the compound was eluted from the plate with methanol, and the product was repurified in the same manner, eluting with 2×10% methanol/methylene chloride. The band at Rf 0.72 was collected, and the title compound was isolated by removal from the silica gel with methanol.

EXAMPLE 31

[Thr]$^2$[O-(4'-Fluorescein-4'-ylmethylaminocarbonyl)-(D)-MeSer]$^3$cyclosporine

[Thr]$^2$[(D)-MeSer]$^3$cyclosporine(28.5 mg, 22.8 μmoles), 1,1'-carbonyldiimidazole (3.3 mg, 20 μmoles), and dimethylaminopyridine (13 μmoles) were combined in DMF (150 L) in a round bottom flask fitted with stirbar and drying tube. The reaction stirred at room temperature for 24 hours. To one-fifth of this reaction mixture was added 4'-aminomethylfluorescein hydrochloride (4.9 mg, 12.3 μmoles) and 4-methylmorpholine (1 drop). The apparent pH was 8–9 by moist pH paper. The reaction was further stirred at room temperature for 24 hours. The volatiles were removed in vacuo, and the residue was taken up into methanol and applied to a 1 mm silica gel plate. The plate was eluted with 15% methanol/methylene chloride. The band at Rf 0.57 was collected, and the title compound was isolated by removal from the silica gel with methanol.

EXAMPLE 32

[(Fluorescein-5-ylcarbonyl)amino Ala]$^8$cyclosporine

[AminoAla]$^8$cyclosporine (obtained from Sandoz AG, Basle, Switzerland; 3.0 mg, 2.5 μmoles), 5-(succinimidooxycarbonyl)fluorescein (Research Organics; 3.1 mg, 6.5 moles), and 4-methylmorpholine (2.0 L, 18 moles) were combined in DMF (100 L) in a stoppered vial equipped with stirbar. The reaction was stirred at room temperature for 2.5 days. The volatiles were removed in vacuo, and the residue was taken up into methanol and applied to a 0.5 mm silica gel plate. The plate was eluted with 15% methanol/methylene chloride. The band at Rf 0.45 was collected, and the title compound was isolated by removal from the silica gel with methanol.

EXAMPLE 33

[epsilon-(N-(Fluorescein-4'-ylmethyl)carboxamidomethylamino-succinyl)-(D)-Lys]$^8$cyclosporine

[N-(Succinimidooxysuccinyl)-(D)-Lys]$^8$cyclosporine (obtained from Sandoz AG, Basle, Switzerland; 3.0 mg, 2.1 μmoles) and 4'-glycylaminomethylfluorescein (1.8 mg, 4.2 moles) were combined in DMF (50 L) with dimethylaminopyridine (5 μmoles) and triethylamine (8.4 moles) in a stoppered vial equipped with a stirbar. The reaction stirred overnight at room temperature. The volatiles were removed in vacuo, and the residue was taken up into methanol and applied to a 0.5 mm silica gel plate. The plate was eluted with 20% methanol/methylene chloride. The band at Rf 0.70 was collected, and the title compound was isolated by removal from the silica gel with methanol.

EXAMPLE 34

[O-(N-(Fluorescein-4'-ylmethyl)-N-propylaminosuccinyl)MeThr]$^{10}$cyclosporine

[MeThr]$^{10}$cyclosporine (obtained from Sandoz AG, Basle, Switzerland; 20 mg, 17 moles), succinic anhydride (27.3 mg, 0.273 mmoles), and dimethylaminopyridine (11.1 mg, 0.091 mmoles) were combined in pyridine (250 L) in a stoppered vial equipped with a stirbar. The reaction was stirred at 45° C. for 3 days. The reaction was taken up into 10 mL of ether and washed with 10 mL of 1N HCl. The aqueous extracts were back-extracted with 5 mL of ether. The combined organic extracts were washed with 5 mL of water and 5 mL of saturated NaCl solution, then dried over anhydrous MgSO4, filtered and concentrated to give 16 mg of [(O-Succinyl)MeThr]$^{10}$cyclosporine, slightly contaminated with the starting material and the bis-succinyl derivative. [(O-Succinyl)MeThr]10cyclosporine (4 mg, 3.1 μmoles) was combined with dicyclohexylcarbodiimide (6 moles), N-hydroxybenzotriazole (6 moles), 4'-aminomethylfluorescein hydrochloride (12 moles), and triethylamine (3.1 μmoles) in DMF (100 L) in a stoppered vial equipped with a stirbar. The reaction was stirred at room temperature overnight. The volatiles were removed in vacuo, and the residue was taken up into methanol and applied to a 0.5 mm silica gel plate. The plate was eluted with 15% methanol/methylene chloride. The band at Rf 0.50 was collected and repurified in the same manner with 2×10% methanol/methylene chloride. The band at Rf 0.2 was collected and the title compound was isolated by removal from the silica gel with methanol.

EXAMPLE 35

[O-AcetylMeBmt]$^1$[O-succinylThr]$^2$cyclosporine

[O-SuccinylThr]$^2$cyclosporine (20.8 mg, 15.8; μmoles) and dimethylaminopyridine (32.5 mg, 0.266 mmole) were combined in acetic anhydride (0.5 mL, 5.3 mmoles) in a round bottom flask fitted with stopper and stirbar. The reaction stirred at room temperature for 3 days. The solution was poured into 0° C. 5% NaHCO3 with stirring, and solid NaHCO$_3$ was added portionwise until the pH of the solution was about 5. The aqueous solution was extracted with 3 portions of ethyl acetate. The combined organic layers were washed with water and saturated NaCl solution, then dried over anhydrous MgSO$_4$. Filtration and concentration gave a residue which was concentrated again from CH$_2$Cl$_2$ and cyclohexane to remove traces of acetic acid. The product was purified on a CHROMATOTRON using a 1 mm rotor and 5–10% methanol/methylene chloride. Fractions containing pure product were combined and concentrated to give 12.6 mg (9.3 μmoles, 58% yield) of the title compound.

EXAMPLE 36

[O-AcetylMeBmt]$^1$[O-(fluorescein-4-ylmethylaminosuccinyl)Thr]$^2$cyclosporine

[O-AcetylMeBmt]$^1$[O-succinylthreonyl]$^2$cyclosporine (5 mg, 3.7 μmoles)was combined with 1-ethyl-3-(3-dimethylaminopropyl)carbodiimide hydrochloride (1.4 mg, 7.3 μmoles) and N-hydroxysuccinimide (1.0 mg, 8.7 μmoles) in 37 μL of methylene chloride and stirred at room temperature overnight. The reaction was taken up into 5 mL of CH$^2$Cl$^2$ and washed with 5 mL of water. The water layer was back-extracted with 5 mL of CH$_2$Cl$_2$, and the combined organic layers were washed with saturated NaCl solution (5 mL) and dried over anhydrous MgSO$_4$, filtered, and concentrated in vacuo. Triethylamine (1.0 L, 7.4 μmoles), dimethylaminopyridine (5 μmoles), and aminomethylfluorescein hydrochloride (2.3 mg, 5.5 μmoles) in DMF (87 L) were added, and the reaction stirred overnight. The volatiles were removed in vacuo, and the residue was taken up into methanol and applied to a 0.5 mm silica gel plate. The plate was eluted with 20% methanol/methylene chloride. The band at Rf 0.83 was collected and the compound removed from the silica gel with methanol. Repurification in the same manner using 1×10 % methanol/methylene chloride gave the product band at Rf 0.74. The compound was removed from the silica gel with methanol to give the title compound.

EXAMPLE 37

[O-(Chloroacetyl)MeBmt]$^1$[O-succinylThr]$^2$cyclosporine

[O-SuccinylThr]$^2$cyclosporine (100.7 mg, 76.4 μmoles) and dimethylaminopyridine (23.1 mg, 0.19 mmole) were combined in chloroacetyl chloride (1.0 mL) in a round bottom flask fitted with drying tube and stirbar. The reaction stirred at 45° C. overnight. The solution was cooled to room temperature and the volatiles were removed on high vacuum. The residue was taken up into l mL of acetone and treated with 1 mL of 1 M NaOAc solution at 0° C. for 1 hour to hydrolyze the acid chloride. The solution was extracted with 20 mL of ethyl acetate. The organic layer was washed with water (2×5mL) and saturated NaCl solution (5 mL), then dried over anhydrous MgSO$_4$. Filtration and concentration gave 105.4 mg. The product was purified on a CHROMATOTRON using a 1 mm rotor and 4.5 methanol/ 0.5% acetic acid/95% methylene chloride. Fractions containing pure product were combined and concentrated to give 53.9 mg (38.6 moles, 51% yield) of the title compound.

EXAMPLE 38

[O-(Chloroacetyl)MeBmt]$^1$[O-(fluorescein-4'-ylmethylaminosuccinyl)Thr]$^2$cyclosporine

[O-(Chloroacetyl)MeBmt]$^2$[O-succinylThr]$^2$cyclosporine (11.3 mg, 8.1 μmoles), 1-ethyl-3-(3-dimethylaminopropyl) carbodiimide hydrochloride (3.4 mg, 17.7 μmoles) and N-hydroxysuccinimide (3.2 mg, 27.8 μmoles), and 4-methylmorpholine (5 L, 45.5 μmoles) were combined in DMF (1.0 mL) in a round bottom flask fitted with stirbar and drying tube. The reaction was stirred at room temperature overnight. One-third of this solution was combined with 4'-aminomethylfluorescein hydrochloride (2.2 mg, 5.3 μmoles). Additional 4-methylmorpholine was added to bring the apparent pH to 8–9. The reaction was stirred at room temperature overnight. The volatiles were removed in vacuo, and the residue was taken up into methanol and applied to a 0.5 mm silica gel plate. The plate was eluted with 15% methanol/methylene chloride. The band at Rf 0.9 was collected and the compound removed from the silica gel with methanol to give the title compound.

EXAMPLE 39

[O-(Azidoacetyl)MeBmt]$^1$[O-succinylThr]$^2$cyclosporine

The procedure of Example 7 was followed, using [O-(chloroacetyl)MeBmt]$^1$[O-succinylThr]$^2$cyclosporine (27.0 mg, 19.3 μmoles),sodium azide (12.7 mg, 0.192 mmoles), and 1.0 mL of DMF. Yield 19.4 mg, 13.8 μmoles, 72%.

EXAMPLE 40

[O-(Azidoacetyl)MeBmt]$^1$[O-(fluorescein-4'ylmethylaminosuccinyl)Thr]$^2$cyclosporine The procedure of Example 37 was followed, using [O-(azidoacetyl)MeBmt]$^1$[O-succinylThr]$^2$cyclosporine (15.2 mg, 10.8 μmoles), 1-ethyl-3-(3'-dimethylaminopropy- 1)carbodiimide hydrochloride (5.8 mg, 30.3 μmoles), N-hydroxysuccinimide (4.8 mg, 42 μmoles), 4-methylmorpholine (4L, 36.4 μmoles), and 4'-aminomethylfluorescein hydrochloride 3.9 mg,9.8 μmoles). The band at Rf 0.87 was collected and the compound removed from the silica gel with methanol. Repurification in the same manner gave a band at Rf 0.85, which was eluted with methanol to give the title compound.

EXAMPLE 41

[(3-(R)-Methyl-5-allyl-2-tetrahydrofuranyl)sarcosyl]$^1$[Thr]$^2$cyclosporine

[Thr]$^2$cyclosporine (50 mg, 41 μmoles) was dissolved in 0.7 mL of dry $CH_2Cl_2$ in a round bottom flask equipped with $N^2$ inlet and stirbar, and cooled to −78 C. with a dry ice/acetone bath. Phenylselenyl chloride (7.9 mg, 41 μmoles) was dissolved in $CH_2Cl_2$ (80 μL) and added dropwise to the cold peptide solution. The reaction was stirred for 25 minutes at −78 C. Meta-chloroperbenzoic acid (8.1 mg, 47 μmoles) was dissolved in 80 L of $CH_2Cl_2$ and added dropwise to the reaction. The dry ice/acetone bath was allowed to come to room temperature as the reaction stirred. After 4 hours the reaction was taken up into EtOAc (10 mL) and washed with 5% NaCO3 (10 mL), 2×5 mL of water, and 5 mL of saturated NaCl solution. The organic layer was dried over anhydrous $MgSO_4$, filtered and concentrated. The residue was purified on 25 g of flash-grade silica gel, using 5% methanol/methylene chloride to elute the column. Fractions containing pure product were combined and concentrated to give 36.7 mg (73.6% yield) of the title compound.

EXAMPLE 42

[(3-(R)-Methyl-5-allyl-2-tetrahydrofuranyl)sarcosyl]$^1$[(O-succinyl)Thr]$^2$cyclosporine [(3-(R)-Methyl-5-allyl-2-tetrahydrofuranyl)sarcosyl]$^1$[Thr]$^2$cyclosporine (36.7 mg, 30.2 μmoles) was combined with succinic anhydride (3.3 mg, 33 μmoles) and pyridine (4.6 L, 60.4 μmoles) in 100 L of DMF in a round bottom flask fitted with stirbar and drying tube. The reaction stirred at room temperature for 4 days. The volatiles were removed in vacuo and the residue was taken up in $CH_2Cl_2$(10 mL) and washed with water (5 mL). The aqueous layer was back-extracted with 2×5 mL of $CH_2Cl_2$. The combined organic layers were dried over anhydrous $MgSO_4$, filtered and concentrated to 20.0 mg of the title compound.

EXAMPLE 43

[(3-(R)-Methyl-5-allyl-2-tetrahydrofuranyl)sarcosyl]$^1$[O-(fluorescein-4'-ylmethylaminosuccinyl)Thr]$^2$cyclosporine

[(3-(R)-Methyl-5-allyl-2-tetrahydrofuranyl)sarcosyl]$^1$[O-succinyl Thr]$^2$cyclosporine (10 mg, 7.6 moles), diisopropylcarbodiimide (1.3 L, 8.4 μmoles), aminomethylfluorescein hydrochloride (3.3 mg, 8.4 μmoles), triethylamine (4.0 L, 28 μmoles) and dimethylaminopyridine (10 moles) were combined in DMF (100 L) in a round bottom flask equipped with a stirbar and drying tube. The reaction was stirred at room temperature overnight. The volatiles were removed in vacuo, and the residue was taken up into methanol and applied to a 0.5 mm silica gel plate. The plate was eluted with 20% methanol/methylene chloride. The band at Rf 0.64 was collected and the compound removed from the silica gel with methanol to give the title compound.

EXAMPLE 44

[O-(Fluorescein-4'-ylmethylaminoformyl)MeBmt]$^1$[O-benzoylSer]3cyclosporine

[Ser]$^3$cyclosporin; 20 mg, 16 moles) was dissolved in pyridine (200 L) in a stoppered vial fitted with stirbar. Benzoyl chloride (2.1 L, 18 μmoles ) and dimethylaminopyridine (5 mg, 41 μmoles ) were added. The reaction was stirred at 45° C. for 2 days. The volatiles were removed in vacuo and the crude reaction mixture was treated as in Examples 3 and 4. The volatiles were removed in vacuo and the residue was taken up into methanol and applied to a 1 mm silica gel plate, which was developed with 1×15% methanol/methylene chloride. The fluorescent band at Rf 0.6 was removed from the silica gel with methanol, and was repurified in the same manner, developing the plate with 2×10% methanol/methylene chloride. The band at Rf 0.3 was removed from the silica gel with methanol to give the title compound.

EXAMPLE 45

[O-AcetylMeBmt]$^1$[O-(fluorescein-4'-ylmethyl)carboxymethylThr]$^2$cyclosporine

[O-(Carboxymethyl)Thr]$^2$cyclosporine(obtained from Sandoz AG, Basle, Switzerland 10mg, 8 μmoles) was dissolved in 200 L of dry methylene chloride. Acetyl chloride (1.7 L, 24 μmoles) was added, and the reaction was stirred at room temperature for 2.5 days. The reaction was taken up into methylene chloride (1 mL), washed with 1N HCl (1 mL) and saturated NaCl solution (1 mL), dried over anhydrous $MgSO_4$, filtered and concentrated to give [O-AcetylMeBmt]$^1$[O-(carboxymethyl)Thr]$^2$cyclosporine. This was then treated as in Example 20, part (a), and as in Example 21. The volatiles were removed in vacuo and the residue was taken up into methanol and applied to a 1 mm silica gel plate, which was developed with 1×15% methanol/methylene chloride. The fluorescent band at Rf 0.6 was removed from the silica gel with methanol to give the title compound.

EXAMPLE 46

Cyclosporine Serum and Whole Blood Fluorescent Polarization Inmmunoassays.

Reagents

The reagents for performing a fluorescence polarization immunoassay according to the present invention were prepared as follows:

(a) Cyclosporine Tracer Reagent:

A 60 nanomolar cyclosporine tracer reagent was prepared comprising the cyclosporine tracer compound prepared according to Example 4 in 0.1 M sodium phosphate buffer, pH 7.5, containing 0.01% (w/v) bovine gamma globulin, 0.1% (w/v) soldium azide, 5.0% (w/v) ethylene glycol and 0.05% (w/v) TWEEN TM 20.

(b) Monoclonal Antibody Formulation:

A monoclonal antibody reagent was prepared comprising mouse (ascites) monoclonal antibody to cyclosporine (Sandoz AG, Basle, Switzerland) diluted with a citrate buffer containing sodium azide.

(c) Pretreatment Reagent:

A pretreatment reagent was prepared comprising 0.1 M TRIS TM buffer, pH 7.5, 0.1% (w/v) sodium azide, 0.5% (w/v) copper sulfate and 10.0% (w/v) 5-sulfosalicylate.

(d) Dilution Buffer:

A dilution buffer was prepared comprising 0.1 M sodium phosphate, pH 7.5, and 0.1% (w/v) bovine gamma globulin.

(e) Serum Precipitation Reagent:

A serum precipitation reagent was prepared comrising 10 mM zinc sulfate in an aqueous diluent with 70% (w/v) ethylene glycol, 25% (w/v) methanol, and 0.5 grams 5-sulfosalicylic acid.

(f) Whole Blood Precipitation Reagent:

A whole blood precipitation reagent was prepared comprising 60 mM zinc sulfate, 50& (w/v) methanol and 30% (w/v) ethylene glycol.

(g) Solubilization Reagent:

A solubilization reagent was prepared comprising 2.0% (w/v) TERGITOL MIN FOAM, 2.0% (w/v) saponin and 0.1% (w/v) sodium azide.

(h) Calibrators:

(1) Cyclosporine monoclonal whole blood calibrators were prepared comprising cyclosporine and an artificial human whole blood matrix. The calibrators were prepared at concentrations of 0.0,100, 250, 500, 1000, and 1500 nanograms per milliliter, with sodium azide as a preservative.

(2) Cyclosporine monoclonal serum calibrators were prepared comprising cyclosporine and a serum matrix. The calibrators were prepared at concentrations of 0.0, 30, 60,120,240 and 400 nanograms per milliliter with sodium azide as a preservative.

(i) Controls:

(1) Cyclosporine monoclonal whole blood controls were prepared comprising cyclosporine and an artificial human whole blood matrix. The controls were prepared at concentrations of 150, 400 and 800 nanograms per milliliter, with 0.1% sodium azide as a preservative.

(2) Cyclosporine monoclonal serum controls were prepared comprising cyclosporine and a serum matrix. The controls were prepared at concentrations of 45, 90 and 320 nanograms per milliliter with sodium azide as a preservative.

Cyclosporine Serum FPIA Assay Protocol

A fluorescent polarization immunoassay for determining cyclosporine in a serum sample employing an Abbott TDx® Therapeutic Drug Monitoring Analyzer was performed as follows:

Fifty microliters each of patient serum samples containing cyclosporine, controls and calibrators were pipetted into labeled centrifuge tubes. A pipette was filled with the serum precipitation reagent, purged of air bubbles, and 150 microliters were dispensed into each centrifuge tube by touching the end of the pipette tip to the wall of each centrifuge tube while dispensing the reagent. The centrifuge tubes were then capped and mixed on a vortex mixer for ten seconds and placed into a centrifuge head so that the tubes were evenly distributed so that the centrifuge head was balanced. The tubes were centrifuged for approximately three minutes at 9,500×g until a clear supernatant and a hard, compact pellet of denatured protein was obtained. After centrifugation was complete, each tube was uncapped and the supernatant was decanted into the corresponding sample well of a TDx® Sample Cartridge. Since 150 microliters of supernatant were required to perform the assay in accordance with the preferred TDx® assay procedure, each centrifuge tube was tapped on the edged of the corresponding sample well of the Sample Cartridge in order to recover all of the supernatant.

Figure 2:
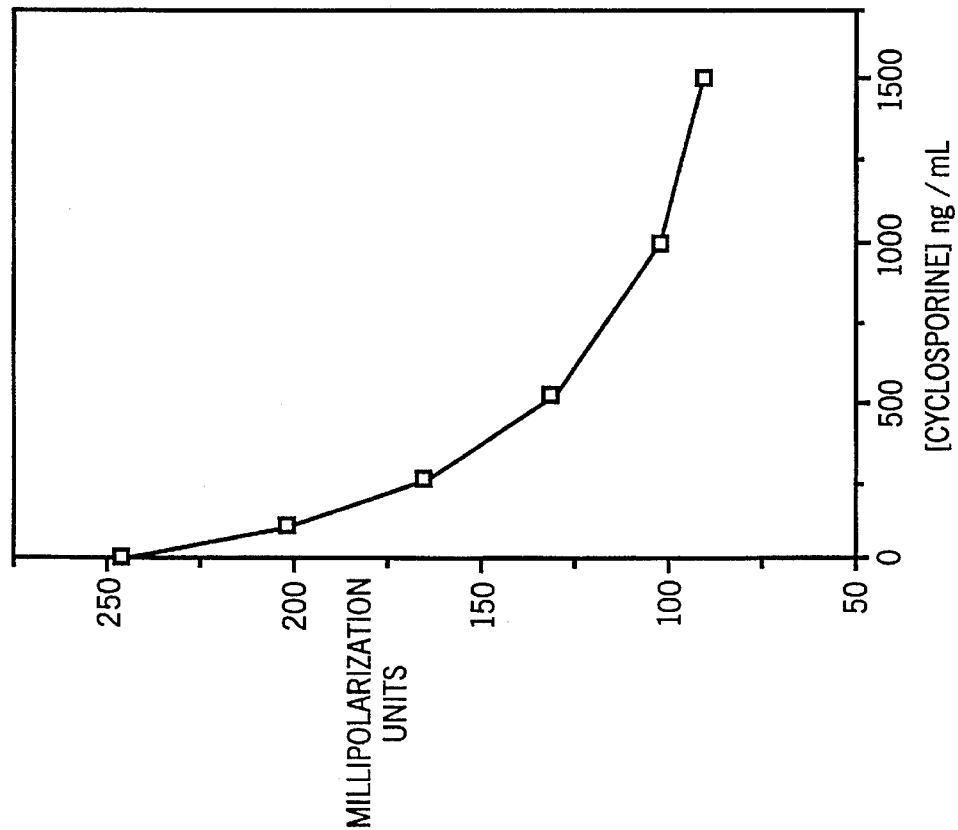
FIG. 2 illustrates a calibration curve employed to determine the amount cyclosporine from a serum sample in a fluorescent polarization immunoassay using the cyclosporine tracer compounds of the present invention.

The fluorescence polarization value of each calibrator, control and sample was determined and printed on the output tape of the Abbott TDx® Analyzer. A standard curve was generated in the instrument by plotting the polarization, P, of each calibrator versus its concentration using a nonlinear regression analysis wherein, the concentration of each control and sample was read off the stored calibration curve (FIG. 2) and printed on the output tape.

The sensitivity of the preferred fluorescence polarization assay according to the present invention is 15.0 nanograms/milliliter of cyclosporine and metabolites. When compared to an available radioimmunoassay using 60 clinical samples, a linear least squared regression analysis gave a slope of 0,947, an intercept of 7.15, and a correlation coefficient of 0,969.

Where a test kit according to the present invention is being used in conjunction with the TDx® Analyzer, the reagents for performing the fluorescent polarization immunoassay according to the present invention can be contained in separate vials of a TDx® Reagent Pack wherein vial caps from each of the vials in the Reagent Pack are removed and placed into designated wells inside the Reagent Pack. Accordingly, once the Reagent Pack is placed inside the TDx® Analyzer, the assay procedure heretofore is fully automated.

If a manual assay is being performed, the test sample is first treated with the precipitation reagent as described above, and then mixed with the dilution buffer. The antibody reagent and the pretreatment solution are then placed into the test tube containing the sample, and a background fluorescence reading is taken. The tracer compound and dilution buffer are added to the sample, and after incubation, a fluorescence polarization reading is taken.

Cyclosporine Whole Blood FPIA Assay Protocol

Figure 3:
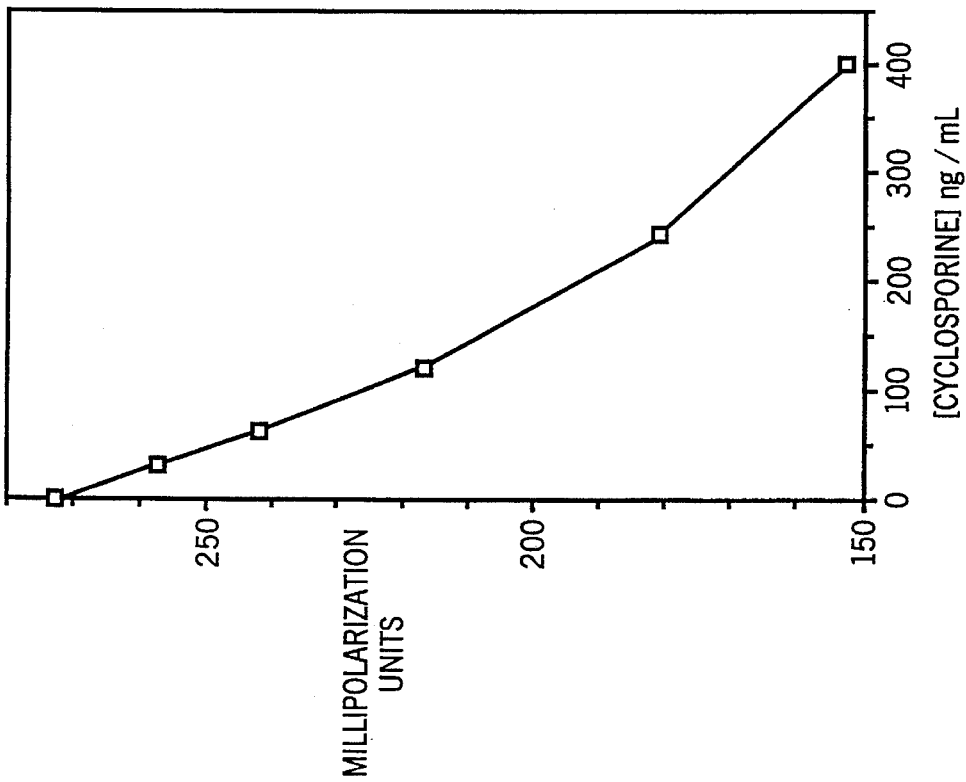
FIG. 3 illustrates a calibration curve employed to determine the amount cyclosporine from a whole blood sample sample in a fluorescent polarization immunoassay using the cyclosporine tracer compounds of the present invention.

A fluorescent polarization immunoassay for determining cyclosporine in a whole blood test sample employing an Abbott TDx® Therapeutic Drug Monitoring Analyzer was performed as follows:

One hundred fifty microliters each of patient whole blood samples containing cyclosporine, controls and calibrators were pipetted into labeled centrifuge tubes, and 50 microliters of the solubilization reagent were added to each of the tubes. A pipette was filled with the whole blood precipitation reagent, purged of air bubbles, and 300 microliters were dispensed into each centrifuge tube by touching the end of the pipette tip to the wall of each centrifuge tube while dispensing the reagent. The centrifuge tubes were then capped and mixed on a vortex mixer for ten seconds and placed into a centrifuge head so that the tubes were evenly distributed so that the centrifuge head was balanced. The tubes were centrifuged for approximately three minutes at 9,500×g until a clear supernatant and a hard, compact pellet of denatured protein was obtained. After centrifugation was complete, each tube was uncapped and the supernatant was decanted into the corresponding sample well of a TDx® Sample Cartridge and the fluorescence polarization value of each calibrator, control and sample was determined and printed on the output tape of the Abbott TDx® Analyzer as described above. A standard curve was generated in the instrument by plotting the polarization, P, of each calibrator versus its concentration using a nonlinear regression analysis wherein, the concentration of each control and sample was read off the stored calibration curve (FIG. 3) and printed on the output tape.

It will be apparent that many modifications and variations of the present invention as herein set forth are possible without departing from the spirit and scope hereof, and that, accordingly, such limitations are imposed only as indicated by the appended claims.

We claim:

1. A Cyclosporine derivative corresponding to the formula:

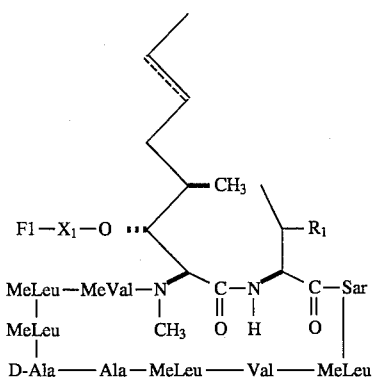

wherein

⇌ represents a single or a double bond

Fl is carboxyfluoresceins;

$X_1$ is a linking group of 1–15 atoms excluding hydrogen;

$R_1$ is hydrogen, OH or $OCOR_6$; and $R_6$ is an alkyl group of from 1–6 carbon atoms or $X_1$–Fl.

2. A cyclosporine derivative corresponding to the formula:

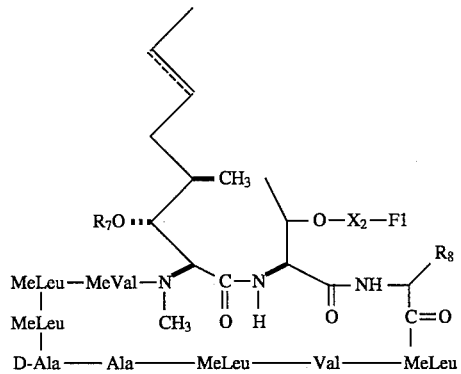

wherein

⇌ represents a single or a double bond $R_7$ is hydrogen or an acyl group of 1–6 carbon atoms;

$R_8$ is hydrogen or $CH_2OR_7$;

$X_2$ is a linking group of 1–30 atoms excluding hydrogen; and

Fl is a detectable moiety from a luminescent molecule selected from the group consisting of fluoresceinamines and carboxyfluoresceins.

3. A cyclosporine derivative corresponding to the formula:

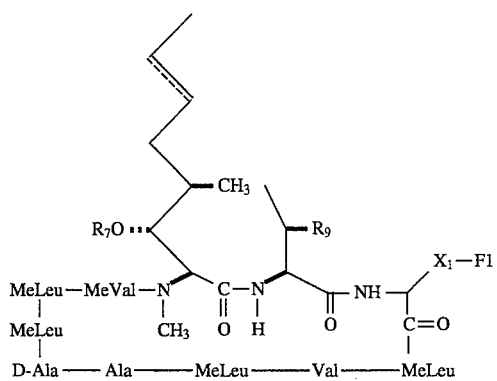

wherein

⇌ represents a single or a double bond $R_7$ is hydrogen or an acyl group of 1–6 carbon atoms;

$R_9$ is hydrogen or $OR_7$;

$X_1$ is a linking group of 1–15 atoms excluding hydrogen; and

Fl is a detectable moiety from a luminescent molecule selected from the group consisting of fluoresceinamines and carboxyfluoresceins.

4. A cyclosporine derivative corresponding to the formula:

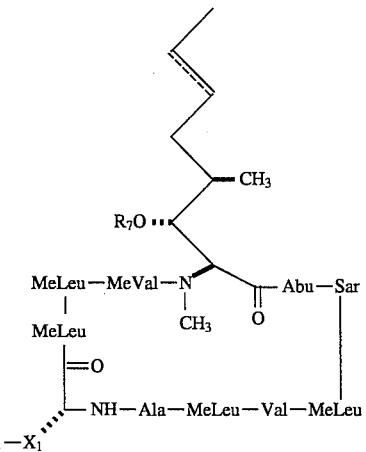

wherein

⇌ represents a single or a double bond $R_7$ is hydrogen or an acyl group of 1–6 carbon atoms;

$X_1$ is a linking group of 1–5 carbon atoms excluding hydrogen; and

Fl is a detectable moiety from a luminescent molecule selected from the group consisting of fluoresceinamines and carboxyfluoresceins.

5. A cyclosporine derivative corresponding to the formula:

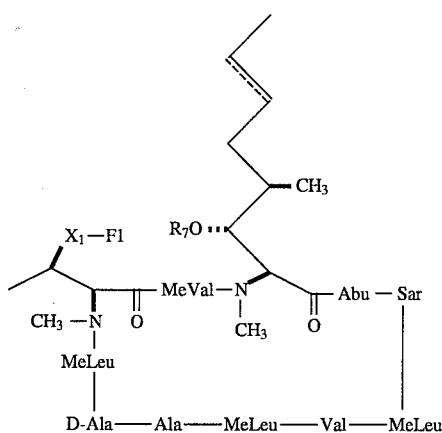
wherein
 represents a single or a double bond
$R_7$ is hydrogen or an acyl group of 1–6 carbon atoms;
$X_1$ is a linking group of 1–15 atoms excluding hydrogen; and
Fl is a detectable moiety from a luminescent molecules selected from the group consisting of fluoresceinamines and carboxyfluoresceins.
* * * * *

UNITED STATES PATENT AND TRADEMARK OFFICE
CERTIFICATE OF CORRECTION

PATENT NO. : 5,489,668  Page 1 of 3
DATED : Feb. 6, 1996
INVENTOR(S) : Morrison, et. Al.

It is certified that error appears in the above-indentified patent and that said Letters Patent is hereby corrected as shown below:

Column 11, line 39, change "TRIS" to --TRIS™--.

Column 12, line 38, change "the application" to --the copending application--.

Column 12, line 42-43, change "polyethylenoxy" to --polyethylenoxy)--.

Column 12, line 44, delete "copending"

Column 15, line 22, change "MgSO4" to --$MgSO_4$--.

Column 15, line 40, change "CHROMATORON" to --CHROMATOTRON--.

Column 23, line 16, change "[(O-succinyl)" to --[O(-succinyl)--.

UNITED STATES PATENT AND TRADEMARK OFFICE
CERTIFICATE OF CORRECTION

PATENT NO. : 5,489,668
DATED : Feb. 6, 1996
INVENTOR(S) : Morrison, et. Al.

It is certified that error appears in the above-indentified patent and that said Letters Patent is hereby corrected as shown below:

Column 23, line 62, change "CH2Cl2" to --$CH_2Cl_2$--.

Column 24, line 36, change "MeBmt]2" to --MeBmt]$^1$--.

Column 26, line 4, change "3cyclosporine" to --$^3$cyclosporine--.

Column 26, line 55, change "TWEEN TM" to --TWEEN™--.

Column 26, line 63, change "TRIS TM" to --TRIS™--.

Column 27, line 11, change "FOAM" to --FOAM™--.

Column 28, line 6, change "0,947" to --0.947--.

Column 28, line 7, change "0,969" to --0.969--.

UNITED STATES PATENT AND TRADEMARK OFFICE
CERTIFICATE OF CORRECTION

PATENT NO. : 5,489,668
DATED : Feb. 6, 1996
INVENTOR(S) : Morrison, et. Al.

It is certified that error appears in the above-indentified patent and that said Letters Patent is hereby corrected as shown below:

Column 30, line 59, change "1-5" to --1-15--.

Column 32, line 11, change "molecules" to --molecule--.

Signed and Sealed this

Twenty-first Day of October 1997

Attest:

BRUCE LEHMAN

Attesting Officer

Commissioner of Patents and Trademarks